(12) United States Patent
Otis et al.

(10) Patent No.: US 10,024,660 B2
(45) Date of Patent: Jul. 17, 2018

(54) METHOD TO DETERMINE PHYSICAL PROPERTIES OF THE GROUND

(71) Applicant: UNIVERSITE DU QUEBEC A CHICOUTIMI, Chicoutimi (CA)

(72) Inventors: Martin Jean-Denis Otis, Chicoutimi (CA); Bob-Antoine Jerry Ménélas, Chicoutimi (CA)

(73) Assignee: UNIVERSITE DU QUEBEC A CHICOUTIMI, Chicoutimi (CA)

( * ) Notice: Subject to any disclaimer, the term of this patent is extended or adjusted under 35 U.S.C. 154(b) by 664 days.

(21) Appl. No.: 14/424,803

(22) PCT Filed: Aug. 26, 2013

(86) PCT No.: PCT/CA2013/050660
§ 371 (c)(1),
(2) Date: Feb. 27, 2015

(87) PCT Pub. No.: WO2014/032181
PCT Pub. Date: Mar. 6, 2014

(65) Prior Publication Data
US 2015/0260514 A1    Sep. 17, 2015

Related U.S. Application Data

(60) Provisional application No. 61/838,014, filed on Jun. 21, 2013, provisional application No. 61/693,494, filed on Aug. 27, 2012.

(51) Int. Cl.
*G01C 22/00*      (2006.01)
*G01B 21/30*      (2006.01)
(Continued)

(52) U.S. Cl.
CPC ............ *G01B 21/30* (2013.01); *A43B 3/0005* (2013.01); *A61B 5/6807* (2013.01); *G01N 19/02* (2013.01); *G01P 15/02* (2013.01); *G01V 9/00* (2013.01)

(58) Field of Classification Search
CPC ... A43B 7/1435; A43B 7/1425; A43B 7/1445; A43B 7/148
(Continued)

(56) References Cited

U.S. PATENT DOCUMENTS 5,635,777 A    6/1997   Telymonde et al.
5,745,055 A    4/1998   Redlich et al.
(Continued)

FOREIGN PATENT DOCUMENTS

EP    2005887 B1       5/2010
KR    20080099752 A    11/2008
(Continued)

OTHER PUBLICATIONS

Otis, Martin J.-D. et al., Toward an Augmented Shoe for Preventing Falls related to Physical Conditions of the Soil, International Conference on Systems, Man and Cybernetics, Oct. 14-17, 2012, pp. 3281-3285, IEEE, Coex, Seoul, Korea.
(Continued)

*Primary Examiner* — An Do
(74) *Attorney, Agent, or Firm* — Norton Rose Fulbright Canada LLP; Alexandre Daoust

(57) ABSTRACT

The method can determine physical properties of the ground stepped upon by a user wearing a footwear incorporating an accelerometer, and includes: receiving a raw signal from the accelerometer during at least one step being taken by the user on the ground; identifying, in the received raw signal, at least one characteristic signature; associating the at least one characteristic signature to physical properties of the
(Continued)

ground; and generating a signal indicating the physical properties based on said association. The generated signal can further be used to advise a user of a risk of falling based on at least the physical properties of the ground.

18 Claims, 14 Drawing Sheets

(51) Int. Cl.
*G01N 19/02* (2006.01)
*A43B 3/00* (2006.01)
*A61B 5/00* (2006.01)
*G01P 15/02* (2013.01)
*G01V 9/00* (2006.01)

(58) Field of Classification Search
USPC .................................. 702/2, 5, 11, 158, 160
See application file for complete search history.

(56) References Cited

U.S. PATENT DOCUMENTS

| | | |
|---|---|---|
| 5,907,318 A | 5/1999 | Medina |
| 6,152,854 A | 11/2000 | Carmein |
| 6,195,104 B1 | 2/2001 | Lyons |
| 6,573,883 B1 | 6/2003 | Bartlett |
| 6,978,684 B2 | 12/2005 | Nurse |
| 7,141,026 B2 | 11/2006 | Aminian et al. |
| 7,340,077 B2 | 3/2008 | Gokturk et al. |
| 7,542,040 B2 | 6/2009 | Templeman |
| 7,632,239 B2 | 12/2009 | Dar et al. |
| 7,683,883 B2 | 3/2010 | Touma et al. |
| 7,714,711 B1 | 5/2010 | Daniel |
| 7,830,359 B2 | 11/2010 | Brush et al. |
| 8,011,229 B2 | 7/2011 | Lieberman et al. |
| 8,195,220 B2 | 6/2012 | Kim et al. |
| 8,244,655 B2 | 8/2012 | Hubbard et al. |
| 8,308,665 B2 | 11/2012 | Harry et al. |
| 8,482,535 B2 | 7/2013 | Pryor |
| 8,644,967 B2 | 2/2014 | Seiler |
| 8,676,541 B2 | 3/2014 | Schrock et al. |
| 8,686,941 B2 | 4/2014 | Rank |
| 8,694,110 B2 | 4/2014 | Nathan et al. |
| 2007/0006489 A1 | 1/2007 | Case, Jr. et al. |
| 2008/0009686 A1 | 1/2008 | Hendrich |
| 2008/0009772 A1 | 1/2008 | Tyler et al. |
| 2008/0186189 A1 | 8/2008 | Azzaro et al. |
| 2008/0281638 A1 | 11/2008 | Weatherly et al. |
| 2008/0318679 A1 | 12/2008 | Tran et al. |
| 2009/0137933 A1 | 5/2009 | Lieberman et al. |
| 2009/0305785 A1 | 12/2009 | Beeman et al. |
| 2010/0035688 A1 | 2/2010 | Picunko |
| 2010/0063779 A1 | 3/2010 | Schrock et al. |
| 2010/0292706 A1 | 11/2010 | Dutson et al. |
| 2010/0299642 A1 | 11/2010 | Merrell et al. |
| 2011/0054359 A1 | 3/2011 | Sazonov et al. |
| 2011/0140897 A1 | 6/2011 | Purks et al. |
| 2011/0148607 A1 | 6/2011 | Zeleny |
| 2011/0199393 A1 | 8/2011 | Nurse et al. |
| 2011/0202306 A1 | 8/2011 | Eng et al. |
| 2011/0242316 A1 | 10/2011 | Guerrero |
| 2011/0251520 A1 | 10/2011 | Shieh et al. |
| 2012/0028577 A1 | 2/2012 | Rodriguez et al. |
| 2012/0092169 A1 | 4/2012 | Kaiser et al. |
| 2012/0095722 A1 | 4/2012 | Ten Kate |
| 2013/0118340 A1 | 5/2013 | D'Amours |
| 2013/0198625 A1 | 8/2013 | Anderson et al. |
| 2014/0156215 A1 | 6/2014 | Eastman et al. |
| 2014/0188431 A1* | 7/2014 | Barfield .................. G01C 5/06 702/160 |
| 2015/0257679 A1* | 9/2015 | Ross ...................... A61B 5/112 702/44 |

FOREIGN PATENT DOCUMENTS

| | | |
|---|---|---|
| WO | 2008058048 A2 | 5/2008 |
| WO | 2008059418 A1 | 5/2008 |
| WO | 2009111886 A1 | 9/2009 |
| WO | 2009156936 A2 | 12/2009 |
| WO | 2010023604 A1 | 3/2010 |
| WO | 2010026513 A1 | 3/2010 |
| WO | 2010128444 A1 | 11/2010 |
| WO | 2010130346 A1 | 11/2010 |
| WO | 2011004322 A1 | 1/2011 |
| WO | 2011133799 A1 | 10/2011 |
| WO | 2011146586 A1 | 11/2011 |
| WO | 2014032181 A1 | 3/2014 |

OTHER PUBLICATIONS

Muaaz, Muhammad et al., Influence of Different Walking Speeds and Surfaces on Accelerometer-Based Biometric Gait Recognition, International Conference on Telecommunications and Signal Processing (TSP), Jul. 3-4, 2012, pp. 508-512, IEEE, Prague, Czech Republic.

Vail, Douglas et al., Learning from Accelerometer Data on a Legged Robot, Proceedings of the 5th IFAC Symposium on Intelligent Autonomous Vehicles (IAV-2004), Jul. 2004, Lisbon, Portugal.

Sim, S.Y. et al., Fall Detection Algorithm for the Elderly using Acceleration Sensors on the Shoes, 33rd Annual International Conference of the IEEE Engineering in Medicine and Biology Society (EMBS), Aug. 30-Sep. 3, 2011, pp. 4935-4938, IEEE, Boston, Massachusetts.

Menelas, Bob-Antoine J. et al, A Serious Game for Training Balance Control over Different Types of Soil, Serious Games Development and Applications, 2012, pp. 31-42, vol. 7528, Springer-Verlag Berlin Heidelberg, Bremen, Germany.

Sprager, Sebastijan et al., Impact of Different Walking Surfaces on Gait Identification Based on Higher-Order Statistics of Accelerometer Data, International Conference on Signal and Image Processing Applications (ICSIPA), Nov. 16-18, 2011, pp. 360-365, IEEE, Kuala Lumpur, Malaysia.

Ben Brahem, Mahmoud et al., Use of a 3DOF Accelerometer for Foot Tracking and Gesture Recognition in Mobile HCI, Procedia Computer Science, 2013, pp. 453-460, vol. 19, Elsevier, Canada.

Bailly, Gilles et al., ShoeSense: A New Perspective on Hand Gestures and Wearable Applications, Proceedings of the SIGCHI Conference on Human Factors in Computing Systems, 2012, pp. 1239-1248, ACM, New York, United-States.

De Sa, Marco et al., Designing and Evaluating Mobile Interaction: Challenges and Trends, Foundations and Trends® in Human-Computer Interaction, 2011, pp. 175-243, vol. 4: No. 3, James Finlay, Hanover, Massachusetts.

Nordahl, Rolf et al., Preliminary Experiment Combining Virtual Reality Haptic Shoes and Audio Synthesis, Haptics: Generating and Perceiving Tangible Sensations Part II, 2010, pp. 123-129, vol. 6192, Springer-Verlag Berlin Heidelberg, Amsterdam, Netherlands.

Tecca, Haptic Shoes Could Help the Blind Navigate Cane-Free, Retrieved from Internet on Jun. 6, 2014. http://news.yahoo.com/blogs/technology-blog/haptic-shoes-could-help-blind-navigate-cane-free-223947138.html.

Ahearn, Nate, Top Spin 3 Review: The best pure tennis game but it still needs some time on the practice court, Retrieved from Internet on Jul. 3, 2014. http://ca.ign.com/articles/2008/06/23/top-spin-3-review-3.

Frazier, Athena, Toward Wearable Pneumatic Haptic Devices for Microscale Force Feedback Applications (Thesis), Jan. 2010, pp. 1-89, Rochester Institute of Technology Kate Gleason College of Engineering, Rochester, New York.

R.E., Fan et al., A Haptic Feedback System for Lower-Limb Prostheses, Transactions on Neural Systems and Rehabilitation Engineering, Jun. 2008, pp. 270-277, vol. 16 Issue 3, IEEE, United States.

* cited by examiner

FIG_4

FIG_8

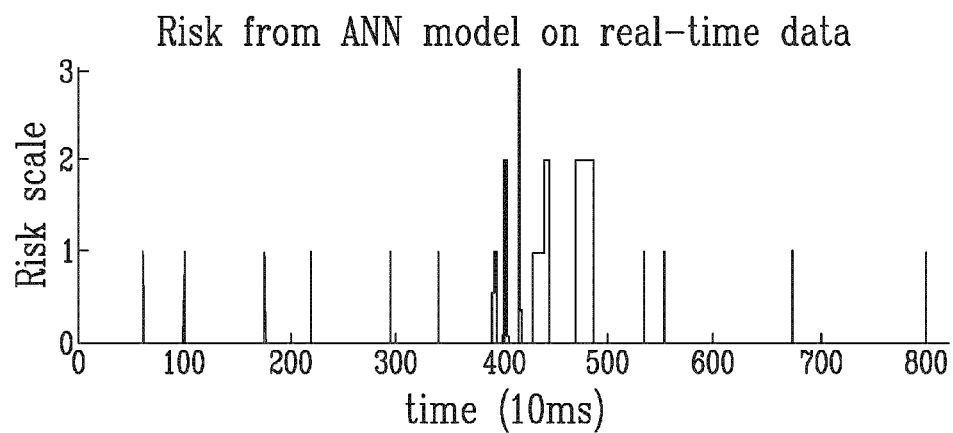
FIG_10A
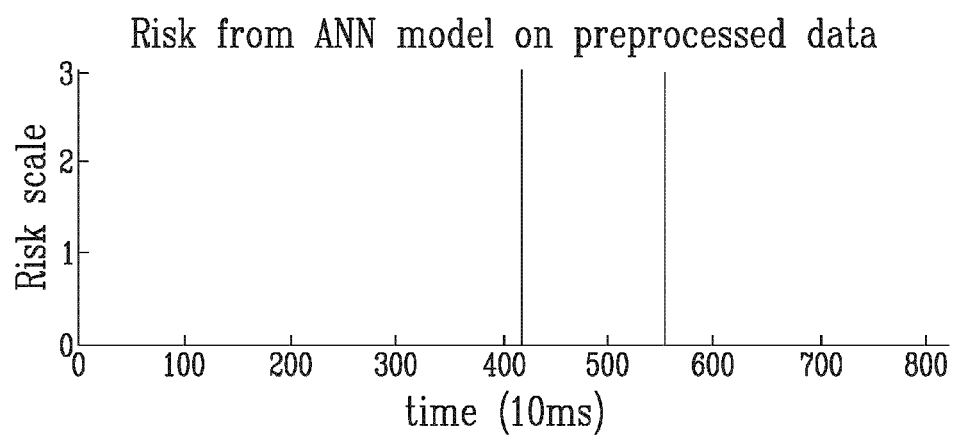
FIG_10B

METHOD TO DETERMINE PHYSICAL PROPERTIES OF THE GROUND

CROSS-REFERENCE TO RELATED APPLICATIONS

This application claims priority of U.S. provisional application 61/693,494, filed Aug. 27, 2012 and of U.S. provisional application 61/838,014, filed Jun. 21, 2013, the contents of both of which are hereby incorporated by reference.

FIELD

The improvements generally relate to the field of wearable devices for interaction with their environment, more particularly in the field of foot-worn devices incorporating accelerometer and indicators.

BACKGROUND

Because of problems that they lead to, programs have been created in order to prevent accidental falls. These programs can target multiple factors that can constitute a certain risk of falling. In this way, several programs have coupled the practice of physical exercises to analysis of balance and gait. Others have been focused on control of vision, hearing and blood pressure. Even though noticeable results have been achieved in this domain, there remains a need for improvement.

SUMMARY

The solution taught herein allows to determine physical properties of the ground that a user is walking on using a signal from an accelerometer located in a foot-worn sensor. By associating physical properties of the ground to property-dependent features of the raw signal of the accelerometer, the foot-worn sensor can detect the type of ground on which the user relies.

Optional features provided by the described embodiment also include means for the system to directly communicate with the user based on the type of ground, or the type of soil information can be used for real-time risk of falling analysis, optionally in combination with other factors.

In accordance with one aspect, there is provided a method of determining at least a physical property of the ground stepped upon by a user wearing a footwear incorporating an accelerometer, the method comprising: receiving a raw signal from the accelerometer during at least one step being taken by the user on the ground; identifying, in the received raw signal, at least one characteristic signature; associating the at least one characteristic signature to at least a physical property of the ground; and generating a signal indicating the physical property.

The solution taught herein allows a user wearing a footwear incorporating an accelerometer to be advised of a risk of falling depending on the type of ground stepped onto. The computing of the risk of falling can be based on physical properties of the ground, characteristics of the environment and on human characteristics.

In accordance with another aspect, there is provided a method for advising a user of a risk of falling influenced by an environment of the ground stepped upon via a footwear incorporating an accelerometer and at least an indicator, the method comprising: receiving a raw signal from the accelerometer during at least one step being taken by the user; identifying, in the received raw signal, at least one characteristic; associating the at least one characteristic signature to at least a physical property of the ground; computing a risk of falling based on the at least a physical property of the ground; and generating a signal in the footwear worn by the user with the at least one indicator, the signal advising of the risk of falling to the user.

In accordance with one aspect, there is provided a ground analysis sensor comprising: a footwear to be worn by a user stepping onto the ground, and an accelerometer sensitive to differences in vibrations depending on the type of the ground, the accelerometer being incorporated to the footwear and emitting an accelerometer signal indicative of the physical properties of the ground when the user steps onto the ground.

Many further features and combinations thereof concerning the present improvements will appear to those skilled in the art following a reading of the instant disclosure.

DESCRIPTION OF THE FIGURES

In the figures,

FIGS. 10a and 10b show examples of results for gait analysis using respectively the ANN-RT model and the ANN-S model;

DETAILED DESCRIPTION

The foot-worn device can be provided in the form of an anklet or a footwear such as a sandal, a shoe, a boot, a sock, a foot wrap or in the sole of this footwear. It will be readily understood that the foot-worn sensor can be provided in the form of a compact electronic device attachable to the footwear or to the foot of the user. Depending on the application, a user may wear one foot-worn device in each foot.

Figure 1:
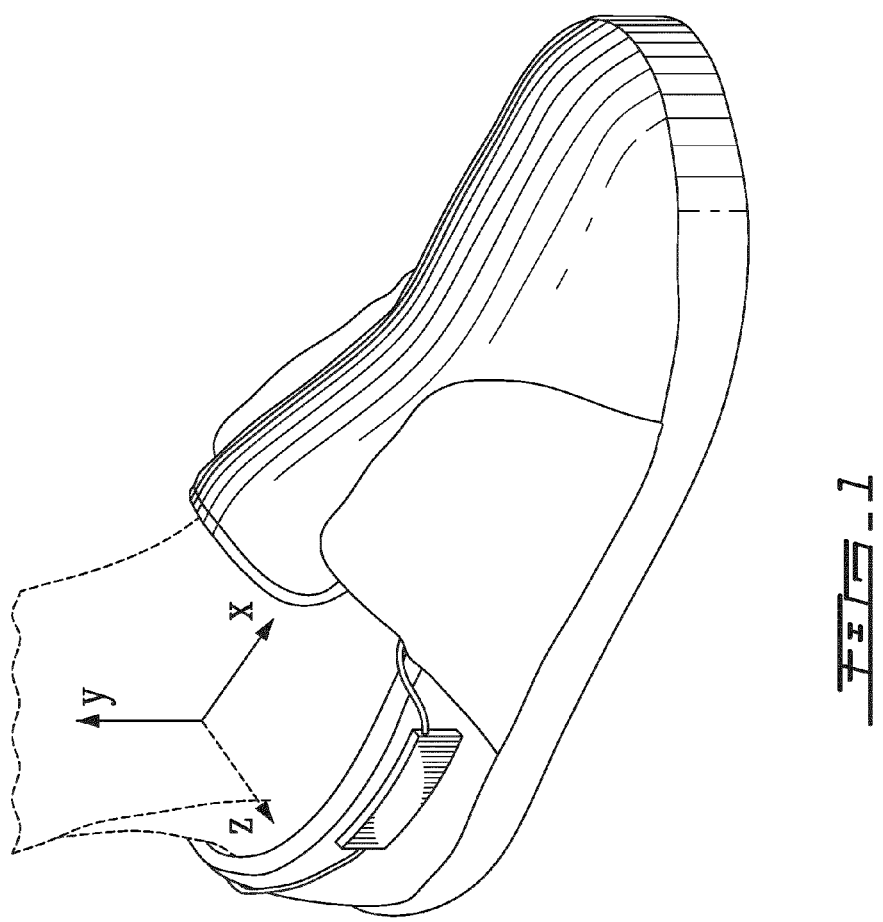
FIG. 1 shows an example of a three axis (x, y, z) referential relative to the footwear.

In a simple embodiment, the foot-worn device can incorporate an inertial sensor, such as a gyrometer or a motion sensor further referred to as an accelerometer. In the preferred embodiment, the three axis accelerometer sensor provides accelerations $a_x$, $a_y$ and $a_z$. As seen in FIG. 1, the referential can be fixed on the accelerometer where the x axis can be forward and backward movements, the y axis can be associated with upward and downward movements, and the z axis can be associated with movements transversely oriented with the direction of the gait, e.g. rightward and leftward movements. In the embodiment described here, the accelerometer should have a sampling frequency above 256 Hz; however, a sampling frequency of about 1 kHz is generally preferable in order to adequately sample the foot gesture of the user.

In another embodiment, the foot-worn device can incorporate indicators provided in the form of acoustic wave generators or haptic indicators, wherein the haptic indicators can be provided in the form of vibratory devices, heat generators such as a resistor dissipating electrical energy, cold generators such as a Peltier cooling module, pinching devices, or any device that is configurable to provide a non-visual feedback to the user or the foot of the user. Each tactile message to the foot of the user wearing the foot-worn device is referred to as a tacton, or tactile icon.

In another embodiment, the haptic indicators are strategically positioned in the footwear. Either on the top of the tongue of the footwear, or in the sole of the footwear. In an embodiment, the haptic indicators can be positioned in a specific pattern in the sole of the footwear. With this later embodiment, pressing the soil with the heel can be distinguished from pressing the soil with the toes, for instance.

In a preferred embodiment, the foot-worn device can incorporate an electronic board incorporating a processor for processing the raw signal of the accelerometer with an identification algorithm in order to determine a physical property of the ground or to advise a user of a risk of falling. The global risk of falling being processed with the processor of the electronic board.

Figure 2:
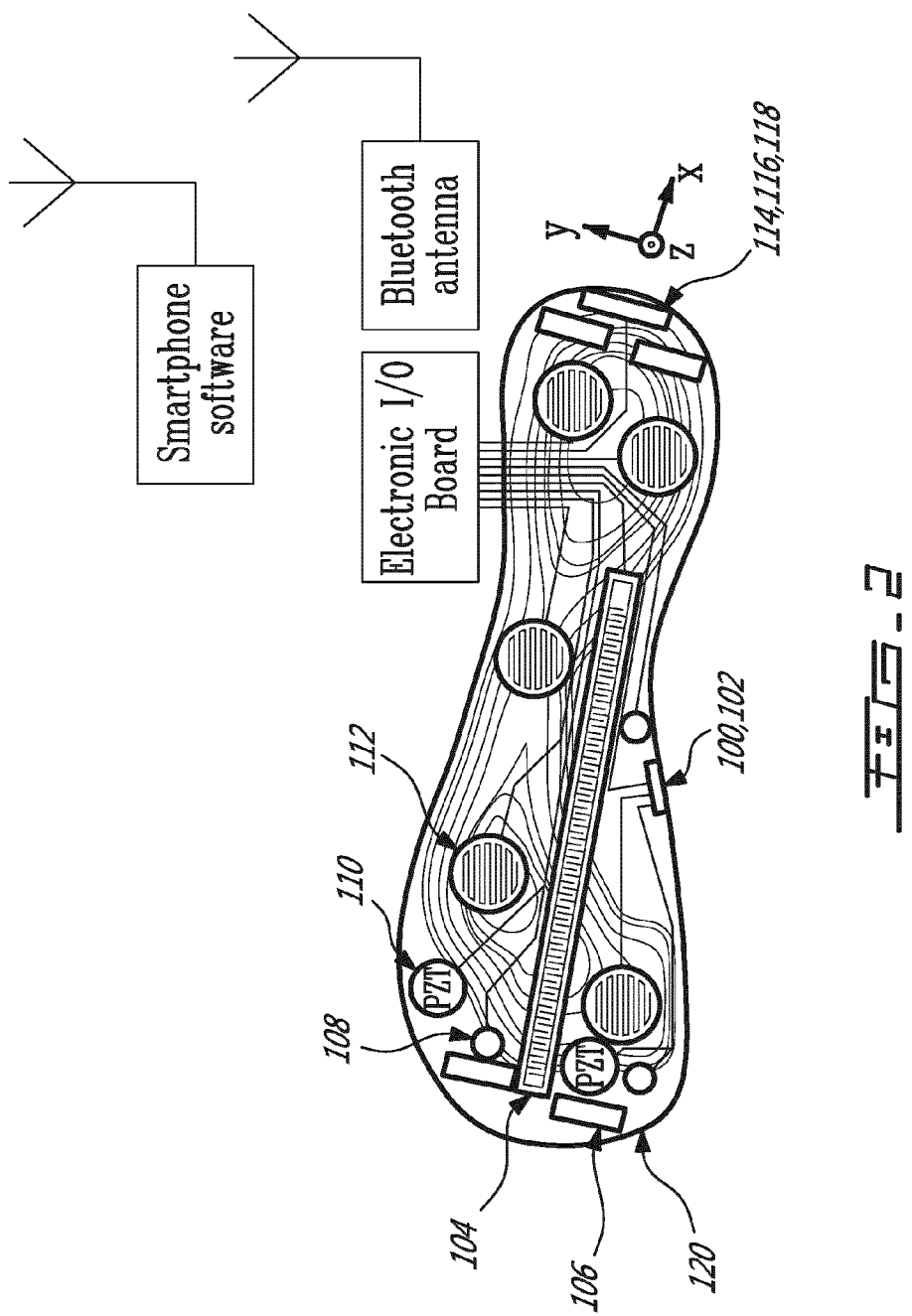
FIG. 2 is a schematic view showing sensor units used on the foot-worn sensor of FIG. 1.

In a more complex embodiment, as shown in FIG. 2, the foot-worn device can comprise a combination of temperature sensors 100, humidity sensors 102, bending variable resistors 104, piezo polymer films 106, haptic indicators such as a vibrating motor 108 and a vibrating actuator 110, force sensors 112 (FSR), gyrometers 114, magnetometers 116 and accelerometers 118 in order to measure other characteristics of the environment with a footwear 120.

Figure 3:
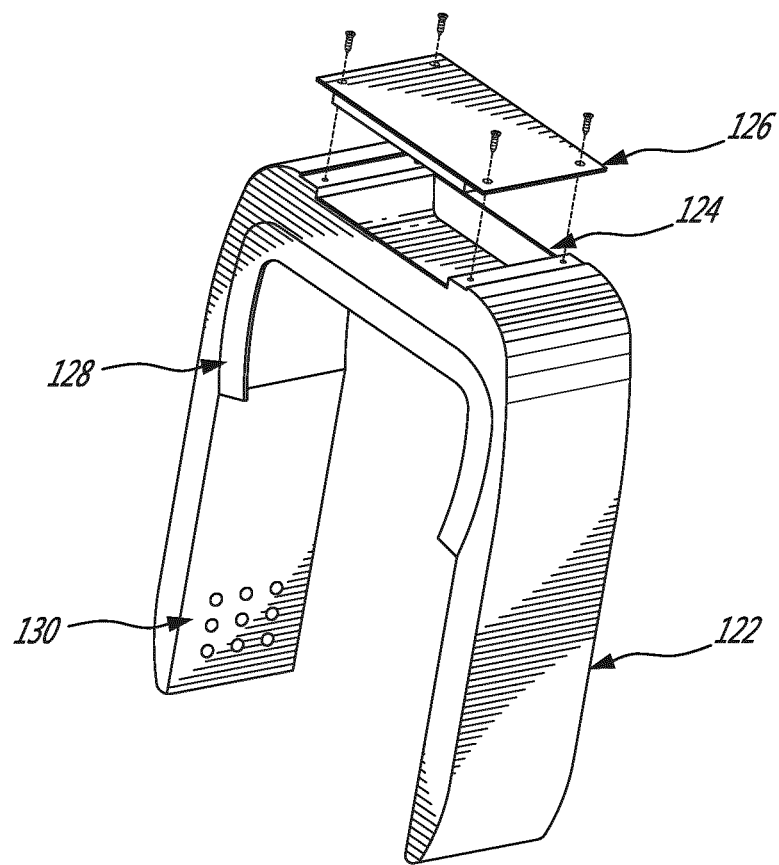
FIG. 3 is a view of the foot-worn sensor incorporable to a heel portion of a footwear.

In order to capture the vibration of the soil, another embodiment is proposed. In this embodiment, the foot-worn device can be fixed of attached to the heel of the footwear of the user in a practical and functional way. The embodiment proposed incorporates the accelerometer and the electronic board without disturbing the user wearing the device, and can fit on any footwear. It gives great stability and simple fixation to the footwear, with constrained degrees of freedom to get better measurement signals. The mechanical device is designed to be fixed externally at the back of the footwear, specifically to the heel part. To satisfy this constraint, a U-shape was chosen with flexible material. Doing so, it can be adaptable with most standard footwear sizes, forms and models (for men, for women, for kids, etc.). An example of this embodiment is shown in FIG. 3. The device can be hold at the heel and is completely fixed for avoiding artifact noise coming from the motion of the device rubbing on the footwear. The selection of plastic considers some parameters such as enough rigidity for reducing damping of the vibration. Two plastic types could be considered: one for the electronic enclosure (rigid and unbending) and the other for the fixation (elastic and flexible).

This embodiment can be composed of two plastic parts. A body 122 for enclosing the electronic circuit and battery in a rigid case 124. A lid 126 to close the electric circuit enclosure of the first part. Both components can be assembled together with four screws.

With such an embodiment, when the first part touches the heel and the surface of the ground, which gives better acceleration measurements. This embodiment enhances the heel motion signature in the raw signal of the accelerometer. Thus, the different gait phases and gait parameters are easily determined to detect eventual gait abnormalities. Also, this embodiment enables the measurement of the ground properties such as vibration, humidity and temperature. One skilled in the art would appreciate that sensors fixed to the side of the footwear tend to lead to noisy measurements.

Furthermore, a metallic band can be added to the embodiment of FIG. 3. The metallic band 128 can provide three functions: (i) enhancement of the transmission of the vibration to the accelerometer; (ii) better grip to wrap the device around the heel of the footwear; and (iii) reduces the plastic material deterioration caused by friction and consequently, increases life time of the device. The metallic band 128 can also be installed under the heel in order to improve the ground contact (heel strike) such that small vibrations could be measured. In short, this metallic band 128 allows transmitting the ground vibrations to the accelerometer, which allow the determination of a ground property type. Additionally, cogs 130 was added at the end of the clips to give additional adherence with the footwear's tissue.

The presented foot-worn device gathers several advantages; including being a transparent and a comfortable wearable device while being not affected by the condition of the environment. More particularly, the foot-worn device can be used anywhere and anytime such as in public transportation means and at the park. Since people generally wear a footwear, it is quite appropriate to think that the foot-worn device can be used in a multitude of situations. Moreover, being mainly incorporated inside the footwear, the foot-worn device disclosed herein can be viewed as a human behaviour helper that can be almost transparent for the user and unperceivable for others. Also, it is of common general knowledge that comfort aspects play an important role when dealing with wearable devices. Accordingly, the foot-worn device is light as it can weigh less than 10% of a footwear. Furthermore, this device does not necessitate any particular attention from the user and it does not represent any danger for the user during use. Regardless of the environment, if it is crowded, noisy, over or under lightened, capabilities of the designed system are generally not to be affected.

Generally, the type of soil can affect the gait, and its differentiation can allow evaluating potentially dangerous situations inside the environment of the user. Variations of the gait of the user may not be enough to obtain a satisfactory indication of risk of falling since a walker can adapt, without any risk, its gait to various human activities. A walker's environment represents the main issue related to fall. The system considers both issues to compute a risk of falling.

One human characteristic which affects the risk of falling is the perception of the ground adhesion or the coefficient of friction. This issue comes from the difference between the current measurement of friction and the psychophysical perception of friction. In fact, a walker can perceive some material properties under the foot while walking. Tactile information like vibration may be used to perceive some material properties like texture, roughness, compliance, and friction. However, vision and audition could be a disturbance on the tactile perception and any coarse evaluation of a slippery surface, for instance, can increase the risk of falling. Furthermore, the human characteristics can depend on the age of the user, its gender, its height, its weight, for instance.

The foot-worn device can also assist in overcoming such disturbances and improve awareness of a walker by providing a clear indication to the user of the type of ground detected by the system. This is assumed via indicators included in the foot-worn device; they allow us to provide tactile or haptic messages to the user.

FIG. 2 shows an example of a foot-worn device, in this particular case a ground analysis sensor, having an accelerometer 118 incorporated in a heel of a footwear 120. As will appear from the description below, the analysis of the raw data captured by the ground analysis sensor can be effected by a separate component, such as an application incorporated into a smart phone for instance, which can be made to communicate wirelessly with the ground analysis sensor via a Bluetooth connection, for instance, or a CPU and software can be directly integrated into the ground analysis sensor, to name another example. In another embodiment, an electronic board incorporated to the footwear can also perform the analysis of the raw data.

In this particular embodiment the ground analysis sensor further incorporates a force sensor 112, the input of which can be used in determining gait parameters (such as establishing contact, midstance, and propulsion of the footwear for instance) useful in processing and/or analyzing the raw signal of the accelerometer as will be exemplified below.

Balance and gait being dependent on physical characteristics of the soil, determination of the physical characteristics of the soil can thus be an important step in providing on-site assistance to a user.

The accelerometer is coupled between the force applied by the whole human body and the ground. The vibration of the ground is derived from the heel strike and the stance phase which could be associated to an impulse response following a Heaviside (step response). Alternately, the measurement can be coupled with heel deformation.

For soils having different physical characteristics, the action of walking will produce differences in the spectral and temporal characteristic signatures of the vibrations occurring between the heel of the footwear and such grounds. The accelerometer is thus used to measure these vibrations and to provide a value indicative of the differentiation thereof in real time.

The differences in the spectral and/or temporal signatures can be subtle between similar ground types, and it was found useful to use an accelerometer which offered sufficient spectral discrimination to analyze this properly. In this example, a system offering a sampling frequency of 1 kHz was found useful to this end.

Four types of ground were used for the experiment in this case of study which could be associated with a corresponding level of risk of falling. This was achieved using a test bench adjacent to a concrete surface. The experiments were conducted on five granular soil types (deformable): broken stone, stone dust, sand, snow and ice. For analyzing the effect of the heel, these granular soils are compared with concrete (considered here as non-deformable). Indeed, concrete may be seen as one particle with a nondominant response of the rheological model compared to the heel response.

A 67 kg man, for who the footwear has been designed, wore the footwear for the experiment. On each surface, he realized about thirteen steps one after the other. During this experiment, for each step the force located at the heel was recorded, the bending of the sole and acceleration at the heel. These measurements are collected at a sampling frequency around 1 kHz which was considered enough for measuring ground reactions and vibrations as shown by the frequency bandwidth in FIG. 4.

Figure 5:
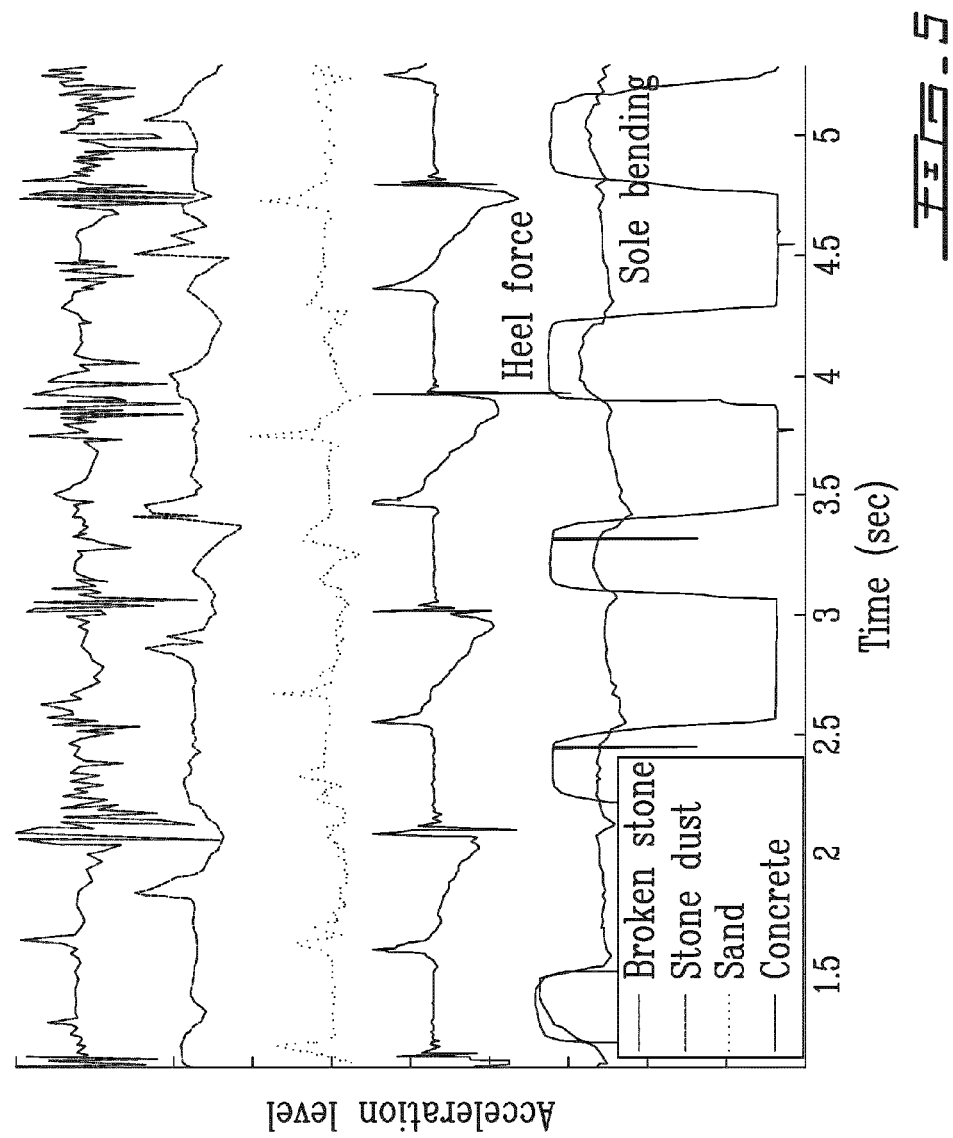
FIG. 5 is a graph showing example of raw signals from the accelerometer obtained from the foot-worn sensor for four types of ground.
Figure 7:
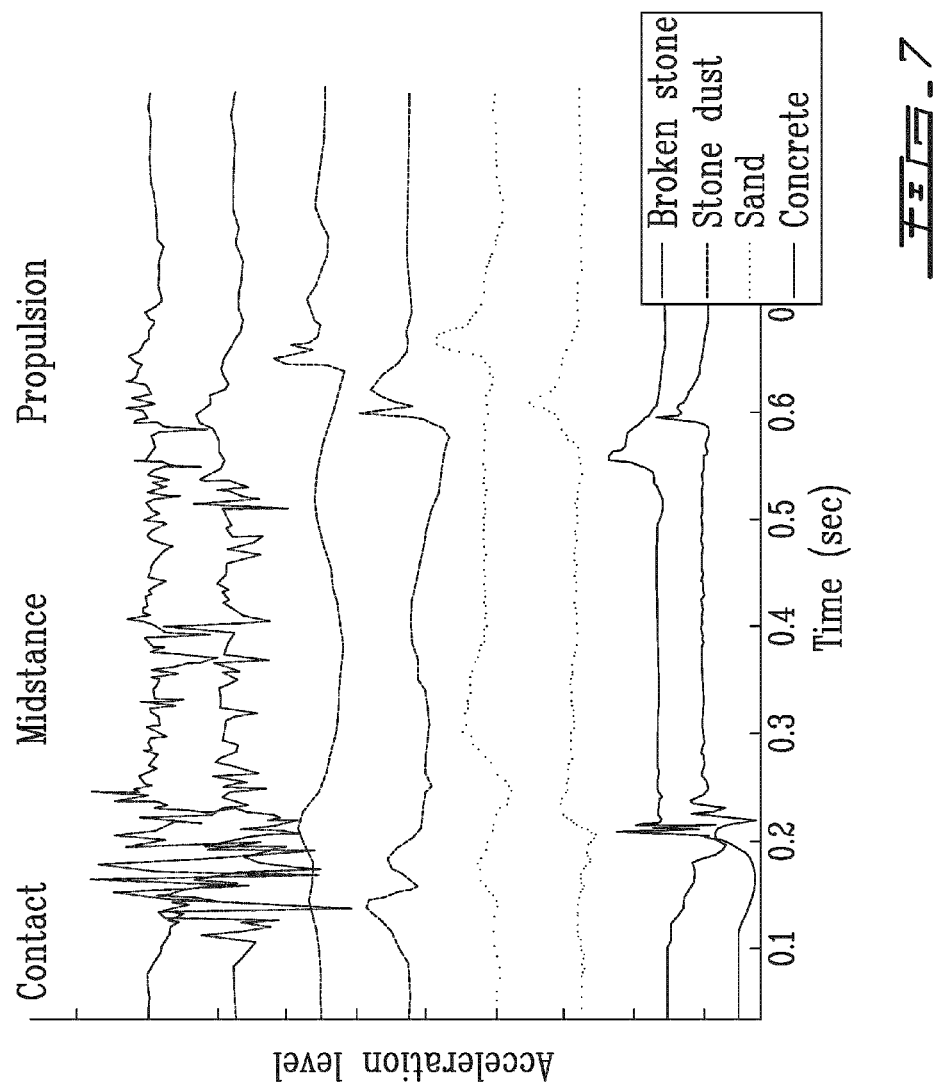
FIG. 7 is a graph showing raw signals after processing with the algorithm of FIG. 6.

FIG. 5 shows a sample of raw signal of the accelerometer collected for the first five steps on the different types of ground. It will be noted that a visible difference is present between these graphs. The difference is explained by the fact that the vibrations measured by the accelerometer represent the variation of the impact force between the footwear sole and the ground. These variations are directly related to the physical properties of the soil. For the three deformable grounds (composed of multiple grains) these properties are characterized by different parameters, and are influenced by the size of a grain and its geometry, the grain density (space available between the grains) and the corresponding rheological model of the soil. These physical properties allow the grains to move when a force is applied by the foot. During movement of the soil, the friction between these grains generates some vibrations. Therefore, these vibrations are a time response of the physical properties of the granular soil excited by the applied force. The heel contact can be correlated to a certain extent with an impact response producing characteristic vibrations detectable with the accelerometer. As opposed to the others, the concrete is a non-deformable ground. It is thus understood that the vibrations corresponding to the impact with this model is significantly different from the previous ones. However, as will be detailed below, with an advanced prototype of the system, not only can non-deformable ground be differentiated from deformable ground, but subtle differences can be used to distinguish three types of non-deformable ground from each other. In FIGS. 5 and 7, the offsets on each measurement are provided to graphically separate each signal to facilitate reading.

Starting from the top of FIG. 5, the four first signals show the raw signal of the accelerometer logged for each type of ground. The two others show the heel force and the bending of the sole (also obtained in this specific example). Looking at the heel force, it is observed that its extrema correspond to equivalent extrema in the acceleration graphs. This let us understand that the data coming from the accelerometer is directly related to the steps performed by the user.

A better understanding of the acceleration waveforms (or raw signal of the accelerometer) needs an insight of the human gait. Human gait is usually composed of two periods in one cycle of walking: stance phase and swing phase. During the stance phase, the muscles are solicited for maintaining balance while during the swing phase; the leg accelerates forward in front of the walker like a double pendulum.

The double stance support occurs between the transition from the stance phase to the swing phase; it represents about 10% of the walking cycle. This name comes from the fact that both feet support the whole body. A walking cycle begins by a double stance support and contains another one after 50% of the cycle. The vibration of the ground is coming from the first heel strike at the beginning of the stance phase. This stance phase has a duration of approximately 60% of the walking cycle. It may be divided into three parts: the first heel strike on the ground (the contact in the initial double stance support), the midstance and the propulsion where the toes apply a force to the ground.

Figure 6:
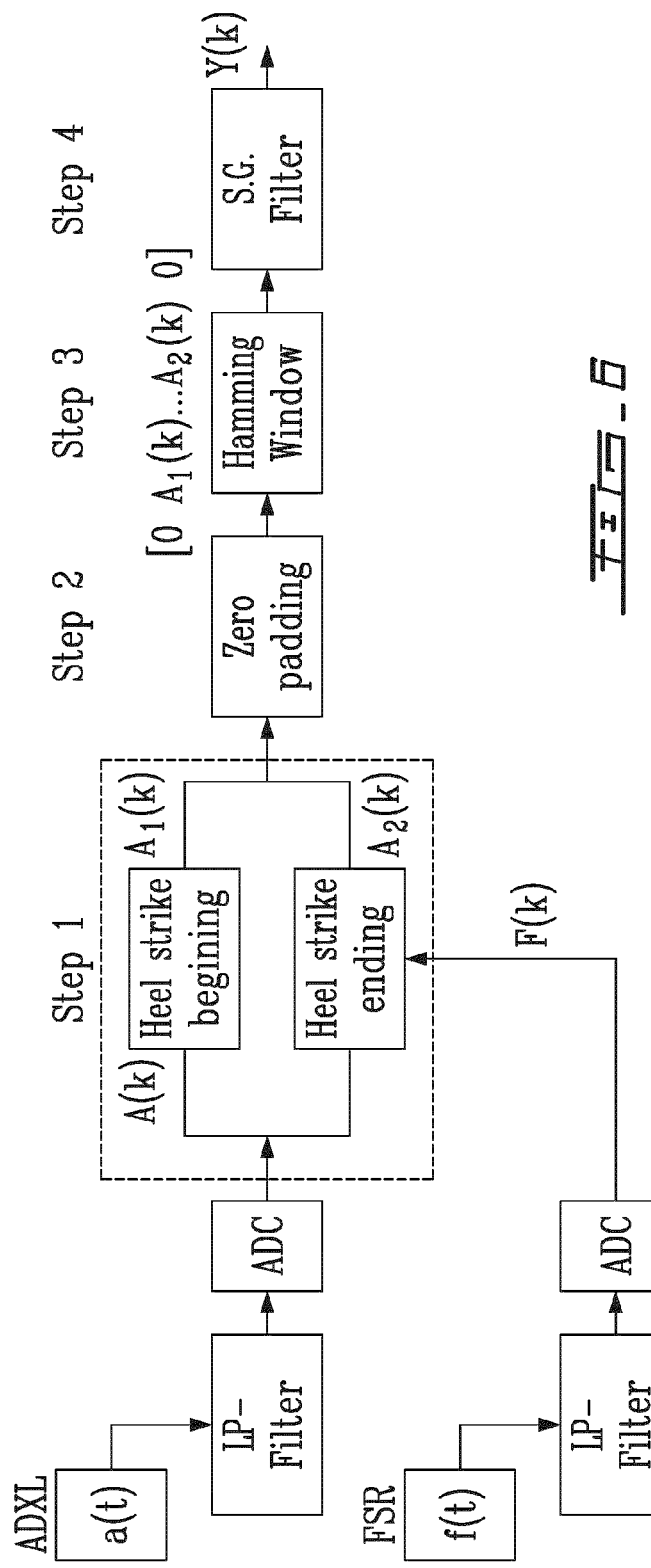
FIG. 6 is an example of an algorithm to obtain and analyse raw signals from the accelerometer.

Waveforms coming from recorded accelerations can be associated with physical properties of the soil. These waveforms can be differentiated through a four steps algorithm as shown in FIG. 6: identification of the beginning and the end of the heel impact on the ground, zeros padding to obtain $2^n$ data points, windowing with a hamming curve and finally filtering with smoothing filter (for example: Savitzky-Golay polynomial fitting or Gaussian smoothing). The beginning and the ending of the heel strike is found more particularly with the FSR force sensor in this case. FSR force sensors help to find the heel strike, but one can use also the acceleration waveform peak instead.

These frames correspond to approximately a second of acquisition associated with the stance phase duration. However, since the duration of the stance phase may vary between gait steps, the number of acquisition points and time are not determined.

The three stance parts are clearly identified on the FIG. 7, where the waveforms clearly exhibit different form of vibration for the different type of grounds.

After the preprocessing step, an index that can differentiate the physical properties in real time is computed. This can be done by analyzing the amplitude and/or timing of vibrations as a function of frequency. In this particular example, a fast Fourier transform (FFT) is used to convert each acceleration waveform coming from preprocessing (as shown in FIG. 7) from the time domain into the frequency domain as shown in FIG. 4.

During this identification, a portion of the raw signal corresponding to a duration of one of the step of the user. Furthermore, it identifies a beginning and an end of the step in the identified portion of the raw signal. In order to properly identify the beginning of the step in the raw signal, a force sensor signal from a force sensor also incorporated in the foot-worn sensor helps to identify a particular phase of the human gait, e.g. the heel strike phase. Once the identification algorithm as found the right portion of the raw signal, it effects a fast Fourier transform (FFT) thereby obtaining the spectral representation of the portion of the raw signal corresponding to the step of the user.

More particularly, once the spectral representation of the raw signal of the step of the user has been obtained, a centroid of that raw signal in the frequency domain is found, wherein the centroid is further associated to the physical property of the ground being stepped onto. Thereafter, a particular type of ground is associated to the physical property determined. Amongst the characteristic signatures possible, one can find characteristic signatures relating to spectral representation, energy computation, time signature and spatio-temporal alignment. Finally, is has to be noted that the physical property of the ground can include a deformability of the ground. For example, for a hard ground like broken stone, the position of the foot can be stable during the stand phase of the human gait, while for a soft ground like sand, the position of the foot can sink through the ground during the stand phase.

Figure 4:
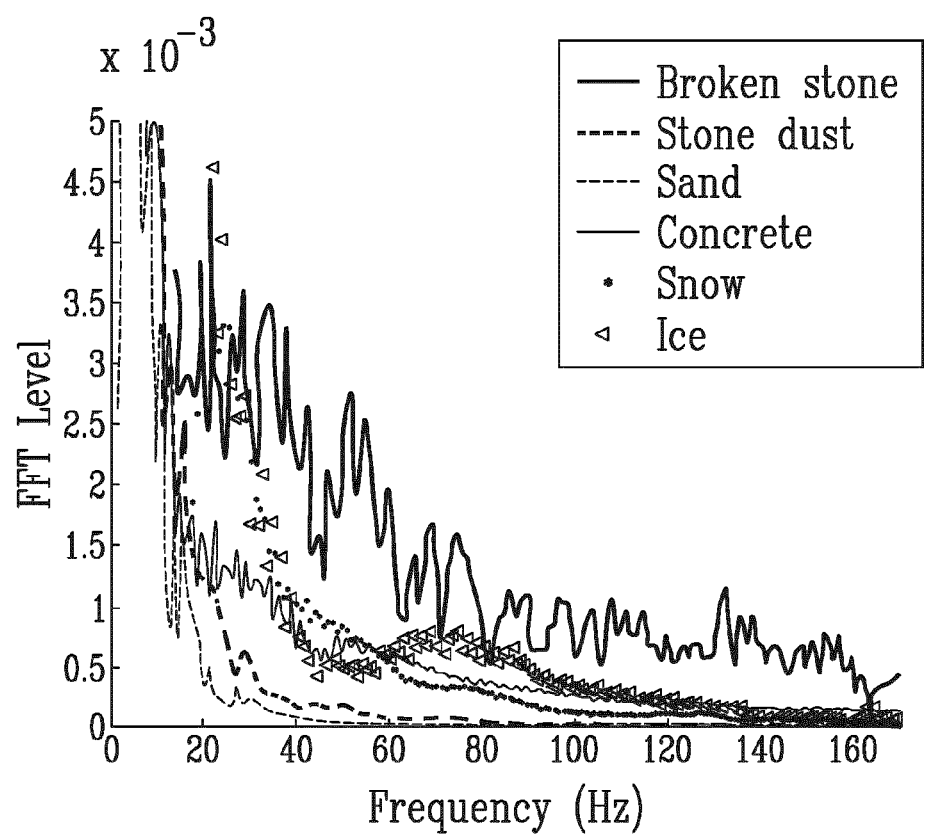
FIG. 4 is a graph showing a spectral representation of the processed signal after using a fast Fourier transform.

FIG. 4 gives the mean absolute value of the FFT for one foot contacts. Thereafter, a centroid of the spectral response is calculated, which corresponds to a value of a characteristic signature in the raw signal of the accelerometer. For avoiding computational burden, a polynomial center is computed along abscissa and ordinate and then divided by the area of the spectral response. This operation may be labeled as spectral centroid and is noted by the coordinate $\hat{x}=(S_x;$ $S_y)$. The centroid of a set of n points masses $m_i$ located at position $x_i$ is computed using:

$$\hat{x} = \frac{\sum_{i=1}^{n} m_i x_i}{\sum_{i=1}^{n} m_i}; \text{ and} \qquad (1)$$

$$\hat{x} = \frac{\sum_{i=1}^{n} x_i}{n}; \text{ where } m = m_i = 1. \qquad (2)$$

Figure 8:
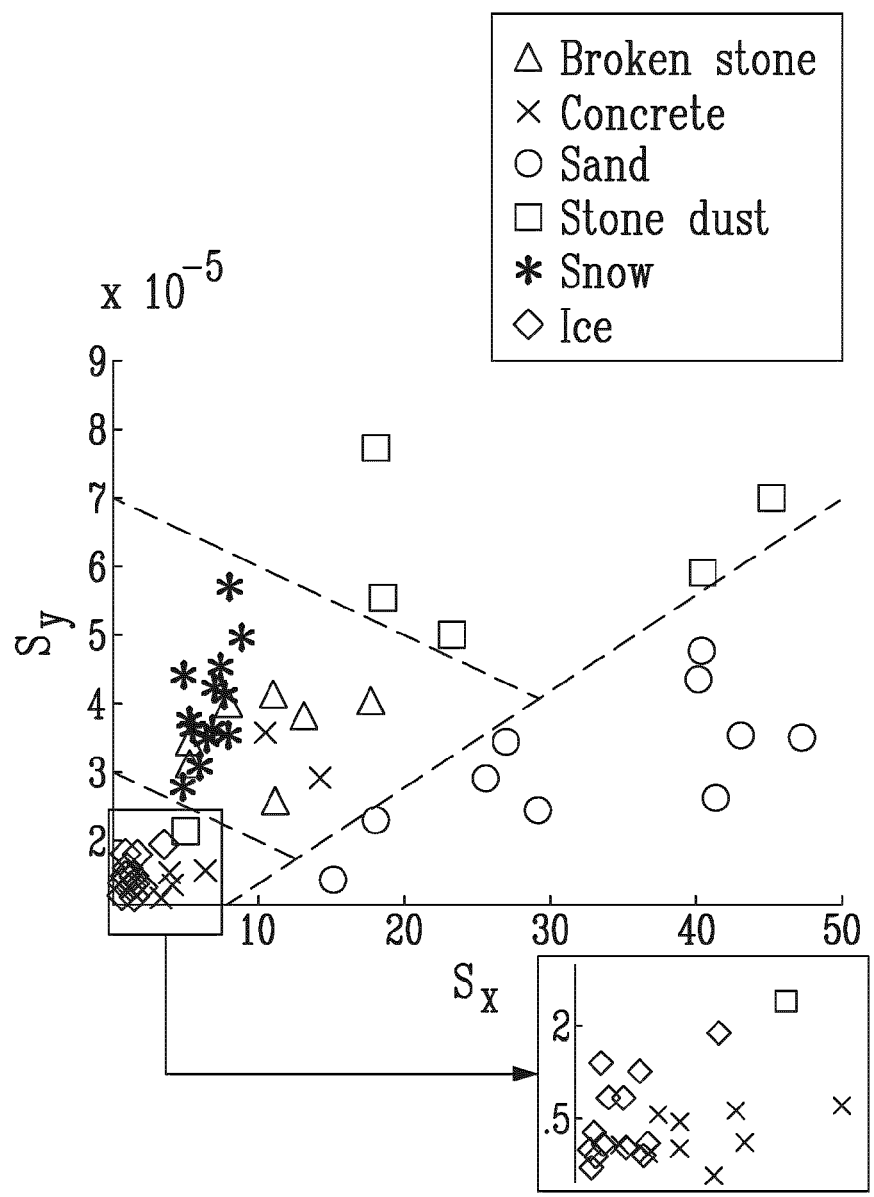
FIG. 8 is a graph that shows centroids of characteristic signatures identified for the x acceleration ($S_x$) and the y acceleration ($S_y$) for the association with a specific type of ground.

FIG. 8 shows the final result of this simple computation. Each data point represents one heel strike. It should be noted that a region of exclusion was defined around a mean response to eliminate some wrong answers. The region of exclusion is defined by the boundary of the figure which corresponds to 50 along the abscissa and $8 \times 10^{-5}$ along the ordinate. As observed, each impact response of a specific soil seems to show a tendency to cluster in a certain region. Using this approach, it has been possible for us to define four clusters such as each region was associated with a specific soil and to associate the centroid, and a characteristic signature in the raw signal of the accelerometer (obtained from the accelerometer sensor) to the ground properties (in this case the ground type). Note that such classification algorithms give a misclassification rate between 1% to 5%, which was considered acceptable. The soil classification will be implemented with the help of fast artificial neural network (FANN). FANN is recognized for its very low computer burden allowing implemented on a smart phone for instance.

To improve the accuracy obtained from the FFT centroid, this product proposes to use features extraction using a simple statistical model. These features are, among others, statistical parameters such as mean, standard deviation, variance, kurtosis, skewness, and energy functions to name a few. Computing a level L for the soil differentiation is achieved by weighted $W_i$ sum of features $F_i$ as follows:

$$L = \Sigma_{i=0}^{n} W_i F_i \qquad (3)$$

Figure 9:
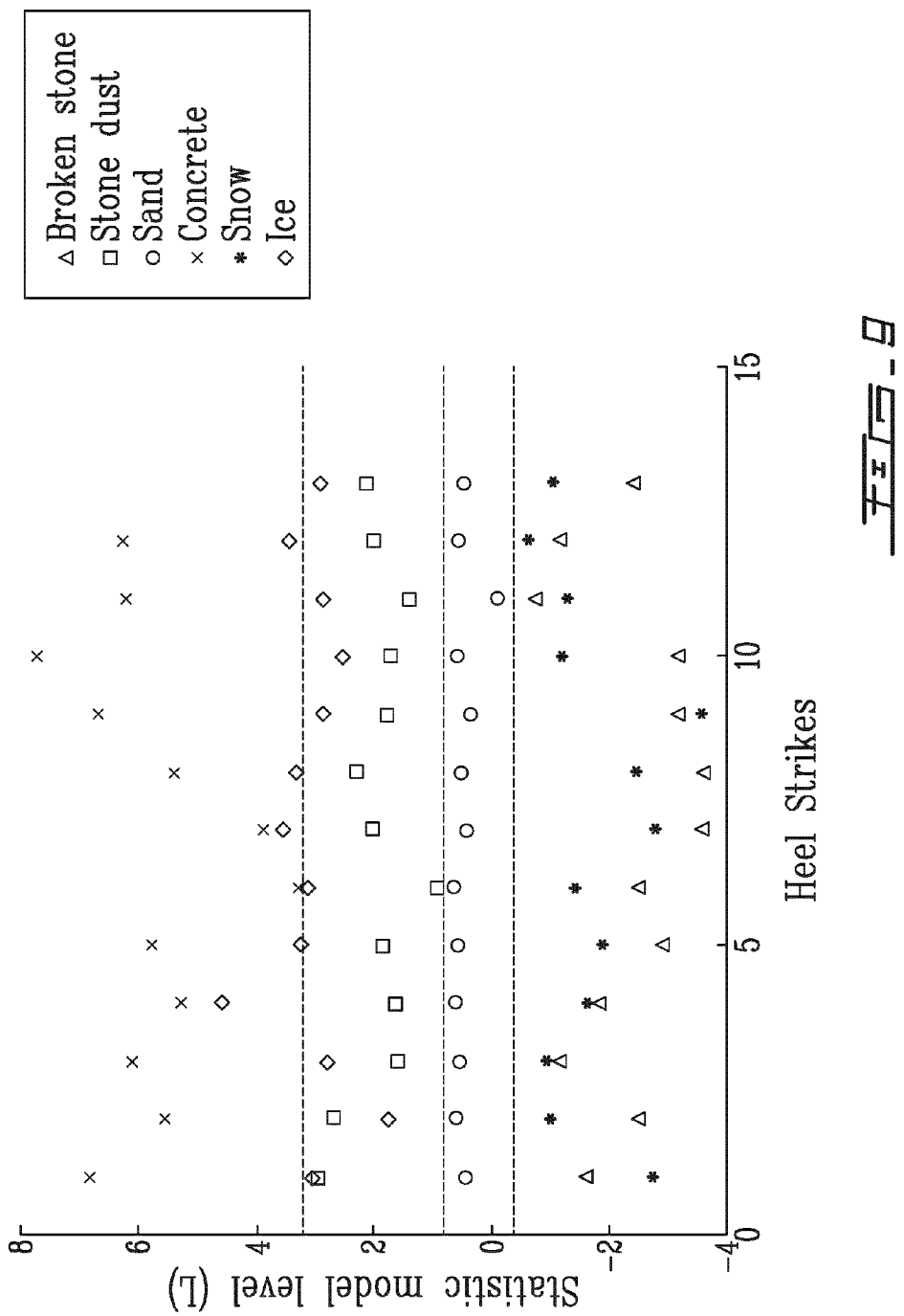
FIG. 9 is a graph that shows the risk level associated to heel strikes for various types of ground.

An optimisation is performed in order to find the best weight values and the best feature combinations. This optimisation is the same as the one used in the artificial neural network for learning algorithm. The results of the differentiation for a multitude of heel strikes for various soil types are shown in FIG. 9. The threshold for the differentiation is then computed using the distance of the mean value between each given soil.

Ice and snow are differentiated using temperature and humidity sensors. As seen on FIGS. 4, 8 and 9, the snow has a similar behaviour than broken stone. Then the level computed here needs further analysis. The preferred method to calculate a risk of falling uses fuzzy logic. The results coming from these figures are fuzzified to consider a broader range of factors affecting the user's behaviour.

Looking at FIG. 8, it is observed that some of the stone dust spectral centroids are situated outside of their associate cluster. One may note that this soil, is the most deformable among the four types experimented. Considering that the response of soil vibrations depends on the force applied by the foot, it is supposed that the soil deformation changes the foot orientation and thus changes the force distribution under the foot. This variation in the force distribution generates an unpredictable response of the soil. It is therefore possible that several spectral centroids be found outside their respective cluster. It will be noted here that optionally, the variation in the force distribution can be measured and identified by the FSR force sensor, in order to evaluate a risk level.

In addition to the simple statistical model presented above, gait analysis can involve two other models: one based on real time data (ANN-RT) and one based on the step of a user (ANN-S). The ANN-RT model generally do not need a full step in order to calculate a risk of falling. However, the raw signal from the accelerometer is not likely to be used without a preprocessing stage. Indeed, in order to calculate a risk of falling with the ANN-RT model, one can preprocess a pressure ratio in a heel portion of the footwear ($R_h$), a pressure ratio under a tip portion of the footwear ($R_t$) and a midstance time ratio ($R_{ms}$). With such a statistical model, the gait analysis can be translated by a risk of falling level. The ANN-S model is similar to the ANN-RT model, except for the fact that the preprocessing stage is performed on an average pressure during midstance ($P_{ms}$) and a stance-to-swing ratio ($R_{sts}$) typically after a complete step of the user.

Since the simple statistical model is a sum of computed data along a step, its curve shows peek waveforms representing gait abnormality. For instance, the simple statistical model can detect a significant difference in the gait parameters, as for regular steps or steps characterized by abnormalities. The first ANN model also treats data along a step, obtaining risk factor according to input features. The model detects mild abnormality during normal walk by providing impulse responses regularly as a function of time. Though, the risk factor augments during the expected abnormalities. Risk evaluated diverges from the simple statistical model as this ANN model seems to adequately spot the start of the abnormal step.

Results of the ANN-RT presented in FIG. 10a. show that the ANN-RT model may give useful information for further analysis on the user's gait monitoring. Despite the fact that the ANN-S model gives the risk of falling evaluation at the end of a step, as showed in FIG. 10b, one could use the result to compute a trend in order to send a warning message to the user. Consequently, this preliminary experimentation on the gait balance gives interesting results and it validates the ability of ANN models to detect abnormal gait. Moreover, different ANNs features obtained from accelerometers may be used to enhance gait evaluation. Furthermore, other methods to obtain data set for ANN training are also in study, including offline simulation of the gait.

Additionally, an experiment was performed in order to determine if a visual perturbation could increase gait abnormalities. For this experiment, users were asked to walk with four types of visual perturbation such as no perturbation ($C_0$), lightly obscured vision ($C_1$), obscured vision ($C_2$) and highly obscured vision ($C_3$). The users were asked to walk along a corridor in a straight line four times; each time wearing different glasses associated with the four visual perturbations. Analysis of the data showed that the three models (the simple statistical model, the ANN-RT model and the ANN-S model) were able to detect gait abnormalities. Furthermore, the models seemed to reveal an increase of the risk level when the visual perturbation was increased. However, other factors can increase the risk level such as external perturbations or uncontrollable variables.

Henceforth, ground properties can be determined using the raw signal of the accelerometer recording the vibrations as a user walks on the ground, as described above. If given soil types are correlated to a given level of risk of falling, for instance, the output of the differentiation and classification algorithms can be attributed a given risk of falling. For example, walking on dry concrete can be determined to correspond to a lowest risk level while walking on soft sand increase the risk to a higher level. The risk associated with each soil type can be attributed according to user preferences for instance.

To bring this reasoning to a further extent, one could represent a surface in accordance with a second order risk model, which gives the risk level for each centroid $\hat{x}=(S_x; S_y)$ computed by equation (1). This surface is the Laplace s-plane and the risk level is computed with the logarithm of the amplitude from placement of the poles and zeros. The user can modify this surface by moving poles and zeros and then adjust the risk level.

In alternate embodiments, the determination of the ground property can be made by using the raw signal of the accelerometer differently. For instance, instead of using a centroid value obtained from a spectral representation of the raw signal of the accelerometer, characteristic signatures of other features can be used such as values relating to energy computation, time-signature parameters, spatio-temporal alignment, statistical calculation (standard deviation, k-means) etc., depending also on the particular application and the available data, and these values can be associated to corresponding ground properties using adapted databases, for instance.

In more evolved versions of the system, it is possible to obtain a more accurate representation of the ground property (ies) using additional sensors. For instance, just using a force sensor as presented above can help in facilitating the automatic identification of the steps and determining the respective timing of vibration events in relation to the user's gait, thereby facilitating the automatization of the signal analysis.

An exemplary, quite evolved, configuration of sensors is shown in FIG. 2. In addition to incorporating an accelerometer 118, and FSR 112, both referred to above, this example configuration goes further and incorporates a plurality of FSRs in the configuration illustrated, a sole bending sensor (bending variable resistor) 104, a temperature sensor 100, a humidity sensor 102, a gyrometer 114 which can be used in conjunction with the accelerometer 118 for the evaluation of gait parameters as stance and swing length, and a magnetometer 116. It can be considered that heel strike and propulsion phases are more related to the risk of falling, in which case, the sole bending sensor can be used to obtain a more representative identification of these phases. Temperature and humidity sensors can be used to identify ice and/or a top layer of water on ice. Humidity sensor can also be used to detect a layer of water on concrete or iron which reduces the coefficient of friction between the soil and the footwear. Magnetometer 116, which coefficient of friction is lower than dry concrete, is used to identify iron, or alloy.

The use of more than one force sensor can allow a fuller insight into the interaction between the foot and the ground, for computation of gait parameters such as center of mass (COM) and center of pressure (COP) in assessing gait stability. The flexion sensor can calculate the angle of the sole and therefore allow assessment of the direction of the wrench vector (force and movement) during propulsion. The indication so provided can be combined with ground property information to evaluate coefficient of friction and, in combination with indication provided by the force sensors, compute wrench boundaries for avoiding slipping on the surface. The piezo-polymer film can be used in sensing dynamic motions and can be used to obtain an indication pertaining to the user's balance when located under the toes, or measure vibrations occurring when the heel is slipping over a surface, for instance, and can be very useful in detecting a situation of imminent fall. The temperature and humidity sensors can be used together in differentiating an icy or otherwise slippery surface from another surface having otherwise similar properties. The gyrometer can be used in conjunction with the accelerometer for the evaluation of gait parameters as stance and swing length. The magnetometer sensors can be used as another input for computing the pose of the foot with the help of a Kalman filter using a fifth order polynomial fitting.

This exemplary configuration goes even further in providing vibrating indicators which can provide feedback directly to the user's foot. Once the risk is assessed, an associated message can be transmitted to the user by the vibrating indicator in the sole. Audible feedback can also be provided, for instance.

The sensors can individually selectively be incorporated directly into the footwear, or made part of a sole, or of a footwear cover, for instance. The use of a sole or footwear cover can be interesting in embodiments where it is desired to retrofit the system to an existing footwear of the user.

Depending on the complexity of the analysis involved, or any other practical considerations, some of the functions of the system can be incorporated on another physical medium than the footwear itself. For instance, the determination of the ground property can be effected by software which can be made part of a smartphone, for instance. In this case, the footwear can have simple electronic means to provide suitable signal acquisition, and include wire or wireless communication means to communicate with the smartphone and its incorporated software. In the embodiment depicted in FIG. 2, this is done via a Bluetooth antenna provided in the footwear. Of course, this can be done using a cable to connect the footwear 120 to the external software, though this may be less practical in many circumstances of intended use. In this embodiment, the signals of the sensors are acquired by an electronic board located in the footwear and which contains an analog-to-digital converter (ADC) and Bluetooth capabilities. The microcontroller on the electronic board embedded in the footwear is a PIC24 from Microchip. Signal waveforms are transmitted via a Bluetooth connection to the smart phone or the electronic tablet, where the data is logged and analyzed in real-time. A preprocessing algorithm is applied on the signal waveforms before the differentiation of ground properties. Subsequent to determination of ground property, and optionally of risk analysis, a message can be sent back to the footwear via the Bluetooth communication channel. Data to be accessed by the software can further be stored in the smart phone's memory.

Figure 11:
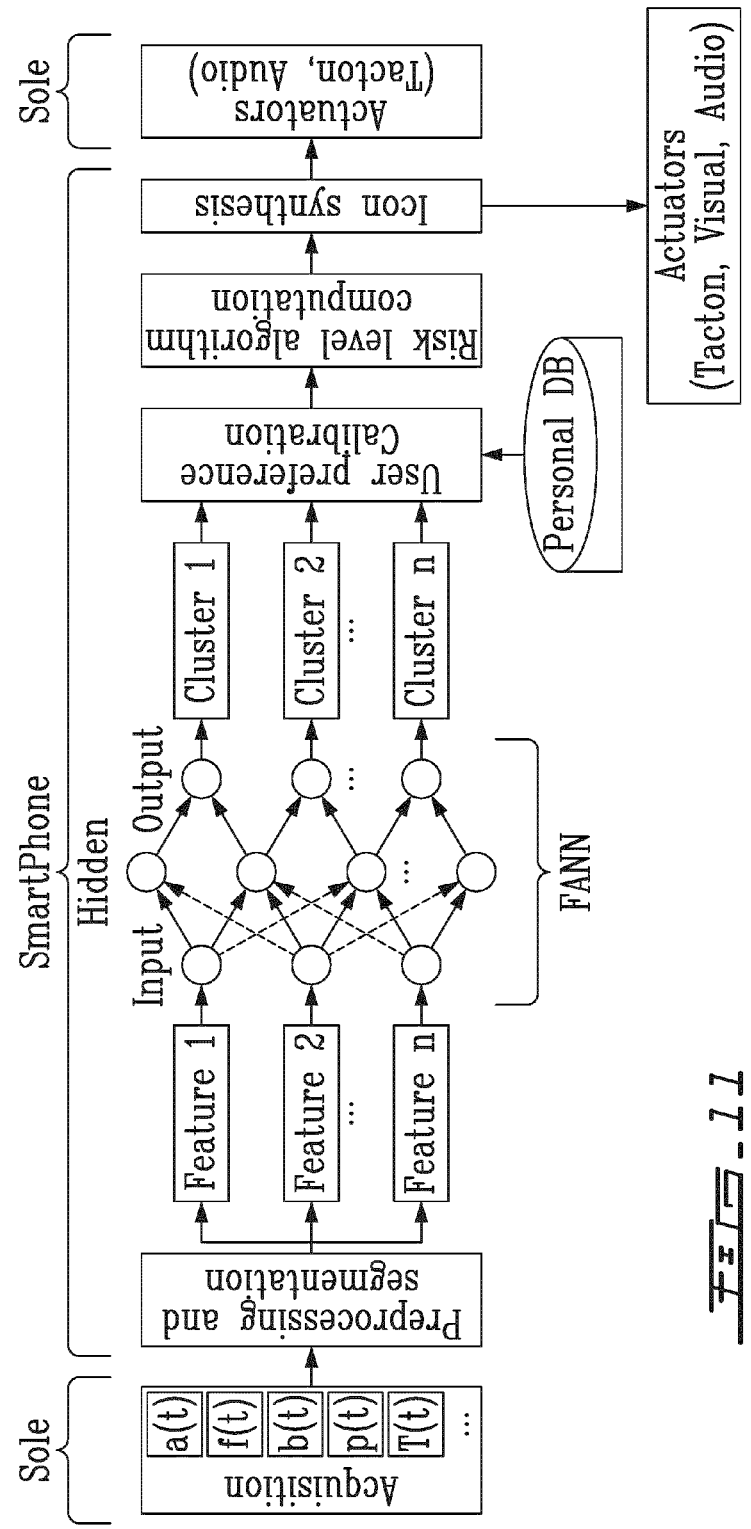
FIG. 11 is a bloc diagram showing an example of an identification algorithm to perform differentiation of ground property types.

An example of the incorporation of the functions in respective components is illustrated in FIG. 11.

In addition to ground type ($R_s$) (or ground properties), other factors can influence the risk of falling in outdoor activities. Software was developed to allow taking risk factors from other sources into consideration in establishing an overall level of risk of falling. Some of the factors can be computed in real-time with the help of the footwear. Such other factors can include the angle of the slope or steep ($R_\theta$), outdoor temperature ($R_{To}$), outdoor humidity ($R_{H\%}$), the user gait as sway posture ($R_G$), the time of walking (standing) associated with the fatigue or exhaustion ($R_t$), atmospheric temperature ($R_a$) and ambient sound or noise (Rs). Others factors depends on the user daily activities or general health. Therefore, this example algorithm for calculation of risk of falling uses a database which contains some factor evaluated off line such as: the type of medication ($R_M$), the fear of falling ($R_F$) and the risk associated with the Berg Balance Scale or Tinetti Assessment Tool ($R_B$). The overall equation for the risk index R is described by (4). The time of walking duration is also a factor which must be evaluated offline for an evaluation of the fatigue or exhaustion effect on balance.

$$R=(R_s R_\theta R_{To} R_{H\%} R_G)(R_M R_F R_B) R_t \qquad (4)$$

The software was programmed to compute a risk index R ranged between 1 and 20. This number is used as a visual indicator on the device on which the software is installed. This risk can be saved in a database for a post-evaluation by a clinician. Each risk factor is also considered independently for the synthesis of an ecological cue. The ecological cue could be visual, vibrotactile or audible depending on the risk of falling.

The risk factors can be summarized as follows for a clearer understanding:

Soil properties ($R_s$): The risk associated to soil properties can be obtained as detailed above.

Angle of the soil ($R_\theta$): As human used to walk on a plane surfaces, walking up or down a slope may increase the risk of falling. An increasing exponential curve was determined to be suitable to evaluate the risk level associated with the angle of the soil. Such an exponential curve can be represented by:

$$R_\theta = 1 + R_0\left(e^{\frac{\theta}{\tau}} - 1\right) - R_0\left(e^{\frac{\theta_0}{\tau}} - 1\right),$$

where $R_0=0.2$, $\theta$ is the soil angle varying from 10° to 90° and $\theta_0=10°$.

Outdoor temperature ($R_{To}$): Frozen soil is a frequent cause of falling and injuries. At high and low temperature, risk of falling is not as high as when temperature is around zero Celsius. At this stage, water film on the frozen soil may lead to slippery surfaces. In this embodiment, a Gaussian curve was used to indicate risk of falling according to the temperature. Such a Gaussian curve can be represented by:

$$R_T = R_{T_0} \cdot e^{\left(-\frac{T^2}{2\sigma^2}\right)} + 1,$$

where $R_{TO}=2°$ C., σ is the standard deviation that can be set up to 3° C. and the +1 is related to a minimum risk level.

Outdoor humidity ($R_{H\%}$): Humidity alone does not increase the risk of falling. Though, captured humidity ratio above the soil may detect presence of a water film. As soil becomes very slippery when wet, high humidity ratio may lead to an increased risk factor. In this embodiment, the sigmoid curve (having a steep increasing slope around 85%) is used to evaluate this risk. Such a sigmoid curve can be represented by:

$R_{H\%}=1+1/(1+e^{-(H\%-If)/2.5})$, where H % is the relative humidity varying between 0 and 100%, If is an inflection point and the arbitrary factor 2.5 is used to tune the slope of the curve.

Fatigue ($R_t$): Walking during for a long continuous period may cause muscular fatigue or awareness fatigue, and this can augment the risk of falling. Here, the sigmoid curve (having a smooth transition of risk level from 1 to 2 from 0 and 30 000 seconds) is used to evaluate how walking time may influence the risk. Such a sigmoid curve can be represented by:

$R_t = 1 + 1/(1 + e^{-(t-tf/2)/3600})$ where t is the time varying from 0 to 28800 seconds (8 hours), for instance and tf is 28800 seconds.

Atmospheric pressure ($R_a$): A low atmospheric pressure is known to reduce motor skills caused by an extension of biological tissues (inflammation) which extends nerves and then cause pain, arthritis symptom is an example. Lower atmospheric pressure also reduces the amount of oxygen available each breath. Also, a high barometric pressure does not usually cause problem, unless it is extreme. For instance, the atmospheric pressure could be measured by a microelectronical system (MEMS) incorporated in the foot-worn device. Thereby, the risk model could be represented by a sigmoid function described by:

$R_a = 1 + 1/(1 + e^{-(A-If)/2.5})$ where A is the atmospheric pressure and If is an inflection point.

Ambient sound or noise ($R_s$): Ambient noise (S) can be measured with a ceramic microphone incorporated in the foot-worn device. The overall energy generated by ambient sounds and measured with the microphone can be computed to find a level of disturbance. One skilled in the art would appreciate that rhythmic sounds decrease gait parameters' variability, however, asymmetric and arrhythmic ambient sounds could affect gait. Consequently, a spectral analysis of the rhythmic patterns of ambient sound could be associated to a risk of falling $R_s$.

Type of medication ($R_M$): Medications can have a dramatic effect on maintaining the balance. Side effects of each drug should be evaluated by a doctor to give them a risk factor. Particular attention should be paid to the combined effects between the drugs. The risk must be updated in the patient record so that the system can consider this factor in the risk calculation. For this reason, drugs increasing risk of falling (DIRF) could be in two classes: benzodiazepines and antidepressants. These medications could also include antiepileptics, antipsychotics, antiparkinsonian drugs, opioids, urological spasmolytics and drugs for cardiovascular diseases.

Fear of Falling ($R_F$): Falls represent a major factor in the frail elderly. Beyond the physical injuries they can cause (fracture of the proximal femur), in many cases falls leave a psychological impact due to the fear of falling. All these factors can lead to a significant loss of autonomy. Fear of falling is also known to be a major factor to increase the risk to fall again. This factor can be obtained from medical records.

Berg Balance Scale ($R_B$): represents the user's ability to maintain balance in different daily situations and can be obtained from medical records.

User gait ($R_G$): Many gait parameters may have an influence on balance. Those parameters include raw data from sensor like the pressure under the foot, the foot bending and the lower body part accelerations (e.g. accelerations on the ankle). Partially process data may also be used as a good gait risk factor indicator. Those include step length, stride length, cadence (number of step per second), stance-to-swing ratio, pressure correlation under the foot and postural sway as well as timing data such as stride, step, stance, swing, and double support time. Models to compute the risk factor according to the patient gait can be based on statistics and on artificial intelligence (AI).

Henceforth, in this embodiment, the software component incorporated to the smartphone further includes databases. The personal database contains personal information of the user. It contains information that will be exploited in order to provide a personalized assistance to the user. In addition to data coming from the footwear, the database can contain data on: fear of falling, daily activities of the user, his medical condition, physical characteristics of its usual environment, characteristics of its lower limbs (morphology) and its gait model (parameters) on different types of ground.

After the computation of the falling risk, indicators incorporated in the system can optionally be used exploited in order to inform the user about the level of risk. Therefore, these signals appear as an aid designed to assist the user. To be useful, rendered signals must be properly assimilated by the user. In other words, in the case of a situation representing a high level of risk in addition to correctly interpret the rendered signal (identify the correct level of risk), the user should not be alarmed by the identified risk level since the stress occasioned by that can lead to a fall. Similarly, in the case of a situation presenting a low risk level, the user should not be less attentive since lack of attention can also lead to a fall. For all these reasons, it seems important to us to pay particular attention to the process of familiarization with the system within a fully controlled environment. For this, software dedicated to the learning of such a signal has been designed.

Figure 12:
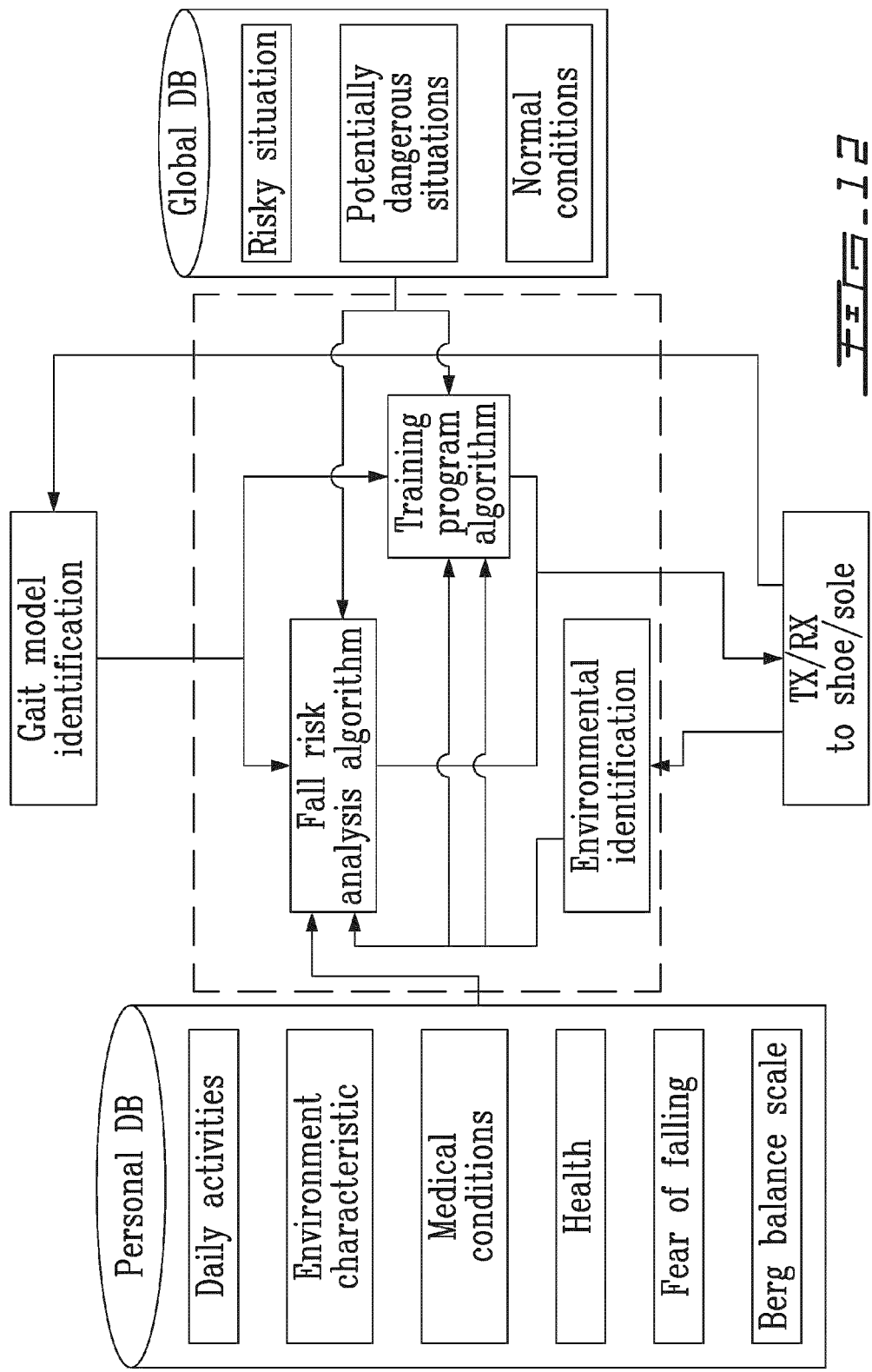
FIG. 12 is a bloc diagram showing components of the software adapted for use with the foot-worn device.

Using these signals to communicate with a person should not prevent him of being fully aware of his external environment. Possible solutions can exploit a channel different than audio or visual. Furthermore, it is known that elderly often do have hearing and/or visual problems. Because of all that, tactile feedbacks for the communication are exploited. The messages are transmitted via the indicators distributed in the footwear. Knowing that humans are not used to exploit these kinds of communication, the user needs to fully understand transmitted messages before any exploitation. This aspect is especially important to avoid all kind of misinterpretation of rendered messages as well as all kind of stress. Therefore a suitable environment was created that can help users at learning transmitted messages. The goal has been targeted through software dedicated to the familiarization, as shown in FIG. 12.

The software used for this purpose can be considered as a familiarization exercise. In this familiarization exercise, the goal of the users is to browsing in a virtual maze as fast as possible and identifying the level of risk associated with each of the areas of the maze while maintaining a normal gait. For this, equipped with the foot-worn device as described above, the user is asked to walk in a real room whose dimensions are mapped those of the virtual maze. This virtual scene can be displayed on the screen of a tablet hand-held by the user. When walking, the player's position in the virtual scene is updated according to his displacements in the real room.

To perform the familiarization exercise several tactons are presented to the player corresponding to its profile. At this first step, he has to select four tactons that will be associated with four levels of risk accordingly (low, medium, high and very high). This design choice is based on studies where it has been showed that there was a strong, positive correlation between preference and successful identification of auditory notifications. After the selection of desired tactons, the user has to browse a virtual maze as fast as possible. When moving, for each area explored the corresponding signal is delivered to the user through the footwear. At each time the user is prompted to identify the level of risk associated with this signal.

To maintain the engagement of the user into the familiarization exercise, several factors to evaluate a score are considered. The score, which aims at evaluating the level of memorization of tactons selected by the user, should be displayed in real-time. Moreover, considering that another purpose of the exercise is about the acceptance of rendered tactons to see if they stress or initiate an unusual behavior to the user, data recorded by an electrocardiogram (ECG) and those concerning the gait of the player can be also analyzed at the end of the session.

One of the main advantages of using a familiarization exercise for learning tactons resides in the fact that the exercise can be experimented at home without the presence of a physiotherapist. However, this raises a number of problems related to user's safety. For this, several design choices were made in order to guaranty the safety of the user. For example, the experimental room should be completely empty in order to avoid accidents. Furthermore, the dimensions of this room can be mapped to those of the virtual room to avoid users banging on the walls. Beyond these aspects, in order to prevent potential injuries, at the end of the analysis performed on the data logged from the ECG and those concerning the gait of the user, if a serious trouble is detected, the familiarization exercise is locked and invites the user to contact the customer service because the familiarization exercise seems to be inappropriate according to his profile.

In order to determine a global risk level, the calculation of the risk of falling involves a risk evaluation algorithm that is based on fuzzy logic, an alternative to binary logic. Indeed, in binary logic, one would need a specific rule to obtain a result, for instance, the variable w is considered "true" (1) for [0, 5] and "false" (0) for ]5, 10]. Consequently, when the variable w is equal to 2, then the value of variable w is "true". Alternatively, in fuzzy logic, the rule would be more sophisticated. For example, the set of rules for fuzzification (or fuzzification relation) would be the variable w is "low" for the relation "0.1 w" and the variable w is "high" for the relation "−0.1 w+1". So, when the variable w is equal to 2, then the value associated to "low" is 0.2 and the value associated to "high" is 0.8 so that one would say that the fuzzy set associated to w is "slightly low" and "fairly high". After the process of fuzzification, one may perform a defuzzification in order to obtain a quantifiable result. In fact, the defuzzification interprets the fuzzy sets into a specific decision or a real value.

Figure 13:
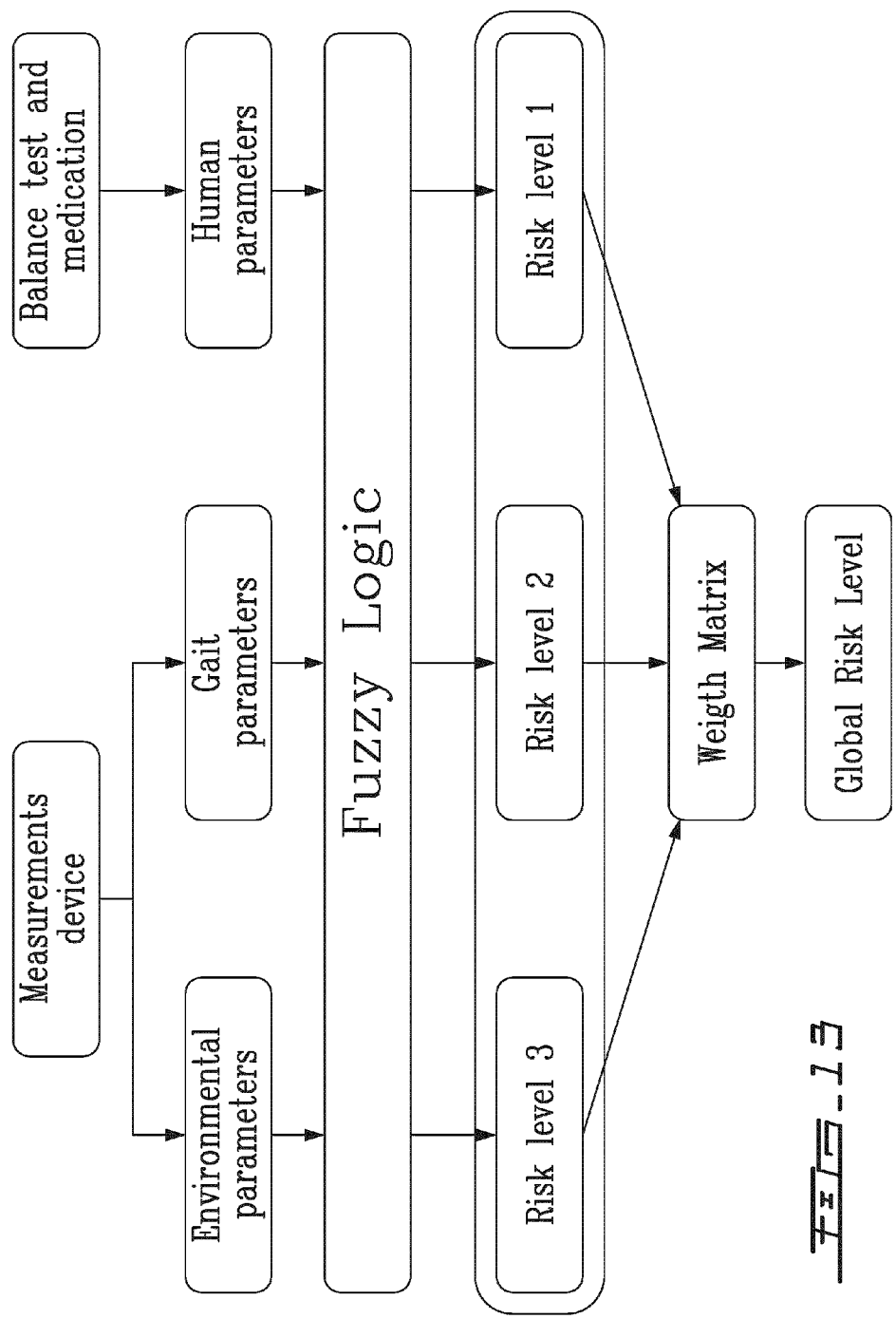
FIG. 13 is a bloc diagram of how fuzzy logic manages the environmental parameters, the gait parameters and the human parameters in order to determine a global risk level.

Typically, fuzzy logic is used for systems having a multitude of input parameter which has to be evaluated to take a decision. Indeed, FIG. 13 shows the bloc diagram of such an algorithm. The risk evaluation algorithm calculates independent risk levels associated with environmental parameters, gait parameters and human parameters (or human characteristics). Once the independent risk levels are calculated, each of them is weighed upon a particular weight (described above) to determine the global risk level. More particularly, the environmental parameters comprise temperature, humidity, soil angle, soil type, walking time and time; the gait parameters comprise cadence, stride length variability and swing time variability; and human parameters can comprise a type of medication, a height, a weight, an age, a gender, a berg balance scale and a fear of falling level. For each of these parameters, fuzzification relations are provided in order to correctly assign the fuzzy sets the parameter.

Figure 14:
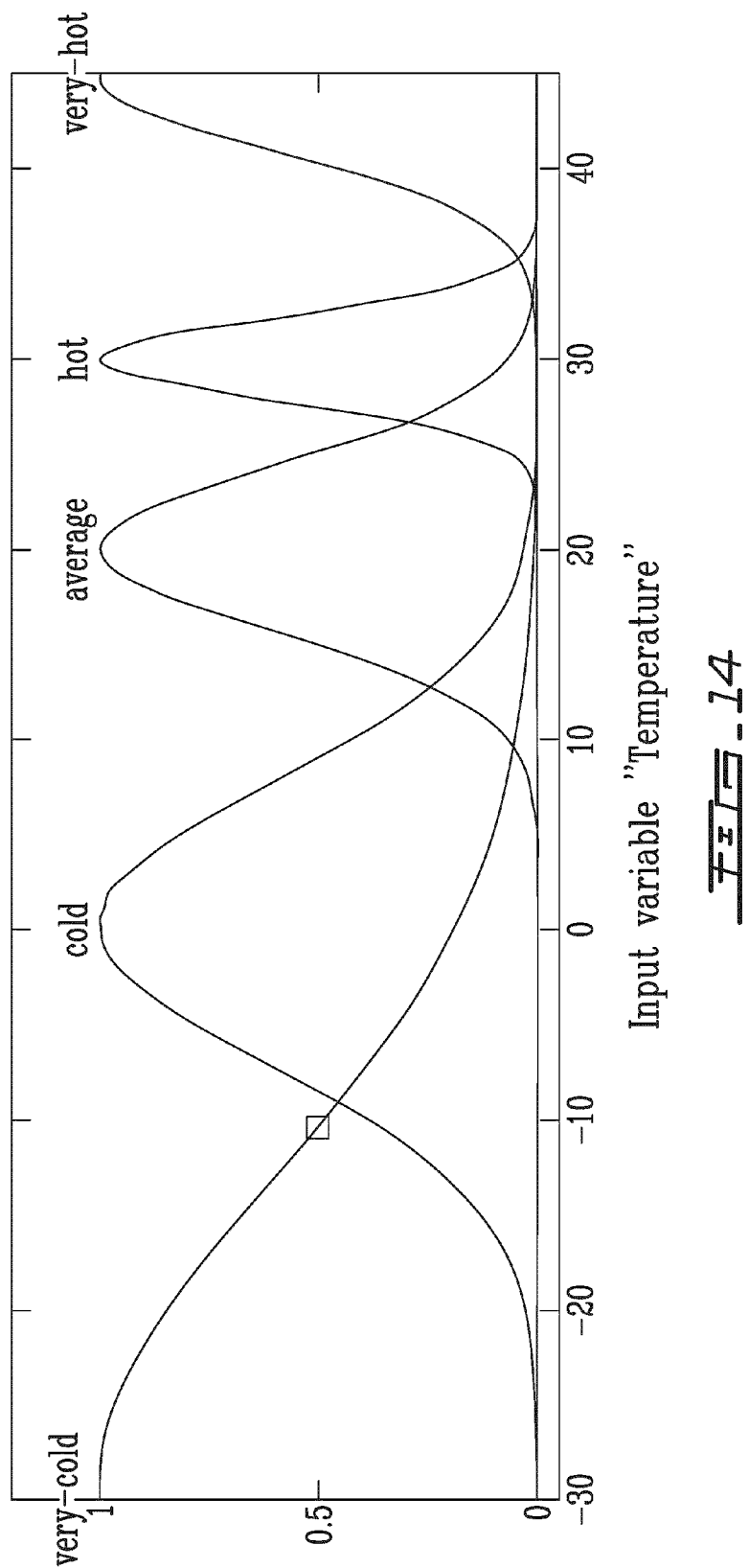
FIG. 14 is an example of a fuzzification relation for a temperature value.

The temperature is a very important parameter that affects the humans gait and the risk evaluation algorithm. Typically, the normal temperature is between 17° and 24°. The range variation of this parameter is [−30° C.; 45° C.]. Since it is a large range, it was divided in five intervals from very cold in the rage [−30° C.; −10° C.[, cold in the range [−10° C.; 15° C.[, average in the range [15° C.; 25° C.[, hot in the range [25° C.; 35° C.[ to very hot in the range [35° C.; 45° C.[, as seen in FIG. 14.

The humidity is also a parameter that can affect the human's gait which can depend of the temperature. The normal supported humidity is between 37% and 53. As humidity is known to change the temperature feeling on one's skin, it affects the risk of falling also. For example, a high humidity percentage increases the temperature feeling (it becomes hotter). However, when the humidity is low it decreases the temperature feeling. The range variation of this parameter is between [0%; 100%]; low humidity between 0% and 37%, average humidity between 37 and 53% and finally, high humidity between 53% and 100%. The slope of the fuzzification relation can include Gaussian curves or triangle functions as well.

The ground slope angle has a direct influence on the human gait depending from the temperature and also from the humidity in the environment. Because these environmental parameters will fix the soil state (dry, wet, etc.). It is considered that from −60° to −30° is a high-descending slope, from −30° to −10° is a descending slope, from −10° to 10° is a plan (no slope), from 10° to 30° is an ascending slope and from 30° to 60° is a high-ascending slope. Increasing and decreasing ground slopes has different risk levels associated to them. The descending slope is considered more dangerous than the ascending slope which can affect the risk variation accordingly. This explains the asymmetric curves around 0° soil angle.

The activity time and intensity during the day can estimate the physical fatigue of the user. Fatigue index helps to evaluate the risk associated to the gait action and conditions. The walking time is classified into three levels: from 0 hour to 1.5 hours (short activity time), between 1.5 and 4.5 hours (average) and more than 4.5 hours (long activity time). The risk is function of the walking time and is linear so the risk increases when this duration increases as well as the activity intensity.

The risk level is also influenced by the time of the day in which the activity is performed and of the activity time described above. Generally, a user is more likely to be tired at the end of the day than at the beginning. For instance, the day was divided in three distinct parts: morning from 8 am to 12 pm, midday from 12 pm to 16 pm and afternoon from 16 pm to 20 pm. Of course, an activity performed in the morning would be characterised by a lesser risk than an activity performed in the morning. In fact, the activity performed in the morning has zero impact of the associated risk level. However, an activity performed at midday is higher than an activity performed in the morning, and an activity performed at midday has a higher risk level if an activity was performed in the same morning. Indeed, an activity performed in the afternoon automatically increases the risk level. If a user had a long activity time in the day, the associated risk level is higher in the afternoon than it would have been with only an average activity time.

The type of soil has also an influence on the gait, and consequently on the risk level. Of course, more a soil is deformable, more energy is necessary at each step and this increases the risk level. Being able to determine a ground property type with the foot-worn sensor helps provide an accurate risk level while a user walk on a particular type of ground. According to the type of ground analysis described above, it is known that the deformability of the ground is influenced by the grain size. Henceforth, the risk level is influenced by the grain size of the soil being stepped onto. Since snow and ice has the same response than broken stone and concrete, respectively, the temperature and humidity can help differentiate ice from concrete, for instance. Generally, even after determination of the ground property type, the associated risk level will vary according to the environmental parameters such as temperature, humidity and ground slope angle. To determine a fuzzification relation for the type of soil, one can use a variable varying from 0 to 1, where 0 is associated to an infinitely deformable soil type and 1 is associated to an infinitely hard soil type. For instance, sand has a value between 0 and 0.2, sand dust has a value from 0.2 to 0.4, stone and snow has a value between 0.4 and 0.8, and concrete, ice, or a soil having a top layer of water on it vary from 0.8 to 1. Of course, differentiating snow from stone, for instance, can rely on other sensors such as humidity sensors or temperature sensors. This differentiation is also used to differentiate a soil having a top layer of water from ice or concrete, for example.

Evaluating the above mentioned environmental parameters in a defuzzification algorithm involves a multitude of rules, some of which are presented in the Table 1.

TABLE 1

Example of rules of the defuzzification process for the environmental parameters.

| Temperature | | Relative Humidity | | Soil Angle | | Walking Time | | Time of the Day | | Risk Level |
|---|---|---|---|---|---|---|---|---|---|---|
| average | & | average | & | plan | & | short | & | morning | so | low |
| very hot | & | low | & | plan | & | short | & | midday | so | average |
| cold | & | low | & | descending | & | average | & | midday | so | high |

The walking cadence, a parameter very similar to the walking speed, can be extracted easily from the raw signal of the accelerometer. The measurement unit for this parameter is the number of steps per minute. For instance, a normal walking cadence for an adult is estimated to 101.8 steps/min. However, it could vary in the range [80 steps/min; 120 steps/min]. The walking cadence depends from very slow from 80 steps/min to 87 steps/min, slow from 87 steps/min to 97 steps/min, average from 97 steps/min to 107 steps/min, fast from 107 steps/min to 115 steps/min and very fast from 115 steps/min to 120 steps/min. For example, when the cadence decreases, the impact on the risk level is more important than when it increases. However, the risk is higher when the walking cadence increases compared with normal average cadence. For instance, five intervals were considered in estimating the walking cadence variation, which are divided by 10 steps/min.

The stride length also influences the risk level. The stride length can be chosen to detect abnormalities in the gait rhythm, which could be a consequence of different environmental or physical parameters such as temperature, humidity, fatigue, and the like. The stride length changes from one user to another, however, the stride length variability is similar for almost all users. Indeed, an increase of 10% of the stride length for a given user is considered to be an eventual gait abnormality. The stride length variability is considered as low from 2.48% to 2.8%, average from 2.8% to 4.7% and high from 4.7 to 5.56%.

The swing time also depends from one user to another. Its variability is helpful to detect gait irregularities. For instance, the swing time is considered to be low from 2.85% to 4.4%, average from 4.4% to 5.9% and high from 5.9% to 7.62%. Also, an increase of 10% in the swing time for a user can significantly influence the associated risk level.

Evaluating the above mentioned gait parameters in a defuzzification algorithm involves a multitude of rules, some of which are presented in the Table 2.

TABLE 2

Example of rules of the defuzzification process for the gait parameters.

| Walking cadence | | Stride Length Variability | | Swing Variability | | Risk Level |
|---|---|---|---|---|---|---|
| very slow | & | low | & | low | so | high |
| slow | & | average | & | average | so | average |
| average | & | average | & | low | so | low |

The independent risk levels are correlated using fuzzy logic in order to obtain the global risk level. The global risk level is divided in three levels: low, medium and high. In another embodiment, there is a possibility to have a state of no danger with a null risk level, however, it is not yet implemented in the output of the fuzzy logic algorithm.

The global risk level is calculated based on the result of the independent risk levels described above: environmental parameters (EP), human parameters (or characteristics) and gait parameters (GP). Once the independent risk levels are calculated, each of them is weighted upon a specific weight, in order to adequately calibrate the global risk level. For instance, the human parameters has a weight of one, while the EP and the GP have a weight according to the Table 3. One is associated to a low risk, two is associated to a medium risk and three is associated to a high risk. One skilled in the art would appreciate that the weight associated with the GP is more important than the one associated with EP or the human parameters, indeed, the GP are more reliable to the risk of falling than the other parameters. The global risk level is estimated from the three independent risk level associated to their corresponding weight.

TABLE 3

Defuzzification curve used to get an intermediate risk level for gait parameters (GP) and environment factor (EP).

| | EP | | |
|---|---|---|---|
| GP | 1 | 2 | 3 |
| 1 | 1 | 1 | 2 |
| 2 | 2 | 2 | 3 |
| 3 | 3 | 3 | 3 |

Considering all these parameters for the risk evaluation, a multitude of rule need to be defined. For example, specific values for the temperature, the humidity, the soil angle, the activity time, the walking time and the soil type can be processed with fuzzy logic in order to obtain a corresponding global risk level.

It will be readily understood that it is possible to obtain the risk level as a function of two or several parameters in the same graph. Accordingly, one skilled in the art could plot the risk level as a function of both temperature and humidity using a standard mesh grid.

As can be seen therefore, the examples described above and illustrated are intended to be exemplary only. The scope is indicated by the appended claims.

What is claimed is:

1. A method of determining at least a physical property of the ground stepped upon by a user, the method comprising:
   stepping onto the ground using a footwear incorporating an accelerometer;
   receiving a raw signal from the accelerometer during at least one step being taken by the user on the ground;
   identifying, in the received raw signal, at least one characteristic signature, said identifying further comprising obtaining a spectral representation of the at least a portion of the raw signal;
   associating the at least one characteristic signature to at least a physical property of the ground; and
   generating a signal indicating the physical property.

2. The method of claim 1, wherein said identifying includes identifying at least a portion of the raw signal corresponding to a duration of one of said at least one step.

3. The method of claim 2, wherein said identifying at least a portion includes identifying a beginning and an end of said at least one step.

4. The method of claim 3 further comprising receiving a signal from a force sensor incorporated in the footwear while the raw signal is received from the accelerometer, and said identifying a beginning and an end of said at least one step in the raw signal is based on the force sensor signal.

5. The method of claim 1, wherein said obtaining a spectral representation includes effecting a fast Fourier transform of the at least a portion of the raw signal.

6. The method of claim 1, wherein said associating further includes associating a type of ground to the at least a physical property determined.

7. The method of claim 1, wherein said at least one characteristic signature has at least one characteristic signature relating to at least one of a spectral representation, energy computation, time signature and spatio-temporal alignment.

8. The method of claim 1, wherein the at least a physical property includes a deformability of the ground.

9. The method of claim 1 further comprising determining a risk of falling of the user based at least on the at least a physical property determined.

10. The method of claim 9, wherein said determining a risk of falling is further based on a determination of variations of the gait of the user.

11. The method of claim 9, wherein said determining a risk of falling is further based on human parameters.

12. The method of claim 9 further comprising activating a haptic indicator incorporated in the footwear of the user based on the determined risk of falling thereby advising the user of a risk of falling.

13. The method of claim 1, further comprising at least one indicator located in the footwear is activatable to communicate the at least a physical property determined to the user.

14. The method of claim 13, wherein at least one of the at least one indicator is an acoustic wave generator generating a sound audible by the user thereby communicating the at least a physical property of the ground stepped onto by to the user.

15. The method of claim 13, wherein at least one of the at least one indicator is an haptic indicator generating vibration to the foot of the user thereby communicating the at least a physical property of the ground stepped onto by the user.

16. The method of claim 15, wherein the haptic indicators are incorporated in the sole of the footwear.

17. A method of determining at least a physical property of the ground stepped upon by a user, the method comprising:
   stepping onto the ground using a footwear incorporating an accelerometer;
   receiving a raw signal from the accelerometer during at least one step being taken by the user on the ground;
   identifying, in the received raw signal, at least one characteristic signature, said identifying further comprising obtaining a spectral representation of the at least a portion of the raw signal, said identifying including converting at least a portion of the raw signal corresponding to a duration of one of said at least one step from the time domain to the frequency domain, and obtaining a centroid of said at least a portion of the raw signal in the frequency domain, wherein said associating includes associating the centroid to a region in the frequency domain corresponding to the at least a physical property determined;
   associating the at least one characteristic signature to at least a physical property of the ground; and
   generating a signal indicating the physical property.

18. A method of determining at least a physical property of the ground stepped upon by a user, the method comprising:
   stepping onto the ground using a footwear incorporating an accelerometer;
   receiving a raw signal from the accelerometer during at least one step being taken by the user on the ground;
   identifying, in the received raw signal, at least one characteristic signature, said identifying further comprising obtaining a spectral representation of the at least a portion of the raw signal;
   associating the at least one characteristic signature to at least a physical property of the ground;
   generating a signal indicating the physical property; and
   determining a risk of falling of the user based at least on the at least a physical property determined, said determining a risk of falling being further based on values of at least one of temperature and humidity sensed in the environment of the ground.

* * * * *